(12) United States Patent
Pagano

(10) Patent No.: US 7,439,032 B2
(45) Date of Patent: Oct. 21, 2008

(54) METHODS TO IDENTIFY COMPOUNDS USEFUL FOR TUMOR SENSITIZATION TO DNA DAMAGE

(75) Inventor: Michele Pagano, New York, NY (US)

(73) Assignee: New York University, New York, NY (US)

( * ) Notice: Subject to any disclaimer, the term of this patent is extended or adjusted under 35 U.S.C. 154(b) by 402 days.

(21) Appl. No.: 10/968,871

(22) Filed: Oct. 18, 2004

(65) Prior Publication Data

US 2006/0177829 A1  Aug. 10, 2006

Related U.S. Application Data

(60) Provisional application No. 60/513,525, filed on Oct. 21, 2003.

(51) Int. Cl.
*G01N 33/53* (2006.01)
(52) U.S. Cl. ........................ 435/7.8; 435/7.23
(58) Field of Classification Search ........................ None
See application file for complete search history.

(56) References Cited

OTHER PUBLICATIONS

Kumar A, Paietta JV. The sulfur controller-2 negative regulatory gene of *Neurospora crassa* encodes a protein with beta-transducin repeats. Proc Natl Acad Sci U S A. Apr. 11, 1995;92(8):3343-7.*
Lin MC, Wright DE, Hruby VJ, Rodbell M. Structure-function relationships in glucagon: properties of highly purified des-His-1-, monoido-, and (des-Asn-28, Thr-29)(homoserine lactone-27)-glucagon. Biochemistry. Apr. 22, 1975;14(8):1559-63. (Abstract only).*

Kipreos et al. The F-box protein family. Genome Biology I(5): Nov. 2000.*
Cenciarelli et al. Identification of a family of human F-box proteins. Current Biology, 9:1177-1179, 1999.*
Ray, D., et al, "Transforming Growth Factor Beta Facilitates Beta-TrCP-Mediated Degredation of Cdc25A in a Smad3-Dependent Manner." Mol. Cell. Biol., Apr. 2005, vol. 25, No. 8, p. 3338-47.
Kanemori, Y., et al, "Beta-TrCP Recognizes a Previously Undescribed Nonphosphorylated Destruction Motif in Cdc25A and Cdc25B Phosphatases." Proc. Natl. Acad. Sci. U.S.A., May 2005, vol. 102, No. 18, p. 6279-84.
Busino, L., et al, "Degradation of Cdc25A by Beta-TrCP During S Phase and in Response to DNA Damage." Nature, Nov. 2003, vol. 6426, No. 6962, p. 87-91.
International Search Report dated Oct. 24, 2006 issued for corresponding International Application NO. PCT/US04/34801.

* cited by examiner

*Primary Examiner*—Larry R. Helms
*Assistant Examiner*—Meera Natarajan
(74) *Attorney, Agent, or Firm*—Darby & Darby P.C.

(57) ABSTRACT

Cdc25A is herein identified as a substrate for β-TrCP1- or β-TrCP2-mediated ubiquitination and subsequent degradation via the ubiquitin-proteasome pathway. In particular, it has been found that interfering with β-TrCP expression or function, or increasing β-TrCP degradation, leads to accumulation of Cdc25A in a cell. Since degradation of Cdc25A is a key feature of the response to DNA damage, leading to a stall in the cell cycle during which the cell can repair the damage, Cdc25A accumulation can abolish this response, thereby sensitizing the cell to DNA damage. Described herein are assays for identifying β-TrCP inhibitors, and method of using such inhibitors for modulating Cdc25A degradation, sensitization of tumor cells, and as adjuvants in cancer therapy based on DNA damaging agents.

10 Claims, 20 Drawing Sheets

|  |  |  | consensus |  |
|---|---|---|---|---|
| SEQ ID NO:9 | βcatenin | WQQQSYLDSGIHSGATT | DSGXXS | SEQ ID NO:20 |
| SEQ ID NO:10 | IkBα | RLLDDRHDSGLDSMKDE | | |
| SEQ ID NO:11 | IkBβ | ADADEWCDSGLGSLGPD | | |
| SEQ ID NO:12 | IkBε | EAEESQYDSGIESLRSL | | |
| SEQ ID NO:13 | EMI1 | ETSRLYEDSGYSSFSLQ | | |
| SEQ ID NO:14 | NFkB1/p105 | RDSDSVCDSGVETSFRK | DSGXXXS | SEQ ID NO:21 |
| SEQ ID NO:15 | ATF4 | EDTPSDNDSGICMSPES | | |
| SEQ ID NO:16 | Cdc25A | RMGSSESTDSGFCLDSPGPLDSK | DSGXXXXS | SEQ ID NO:22 |
| SEQ ID NO:17 | peptide | TDSGFCLDSPGPLD | | |
|  |  | (P)    (P) | | |

| | | |
|---|---|---|
| SEQ ID NO:18 | DSG2x | RMGSSESTDAGFCLDAPGPLDSK |
| SEQ ID NO:19 | DSG3x | RMGSSEATDAGFCLDAPGPLDSK |
| | | 79 82    88 |

Fig. 4

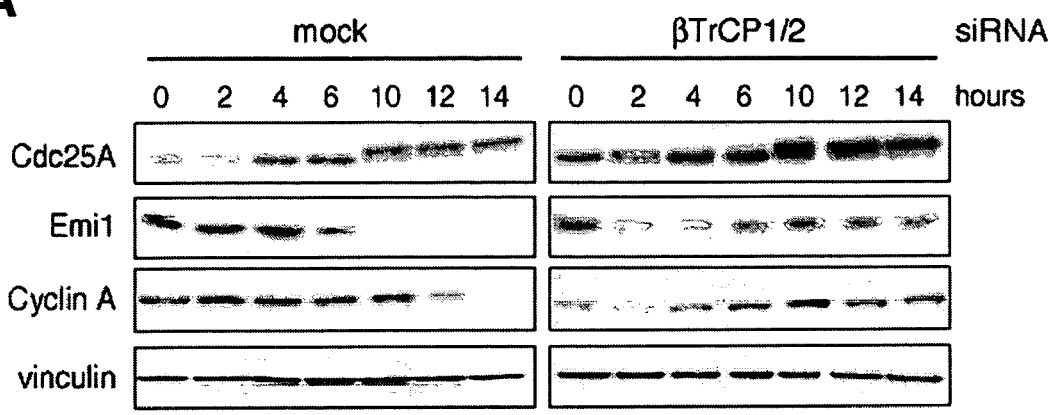
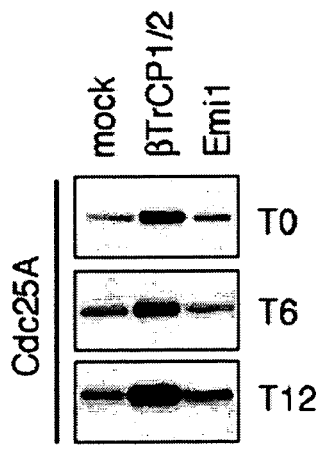
Fig. 12

A
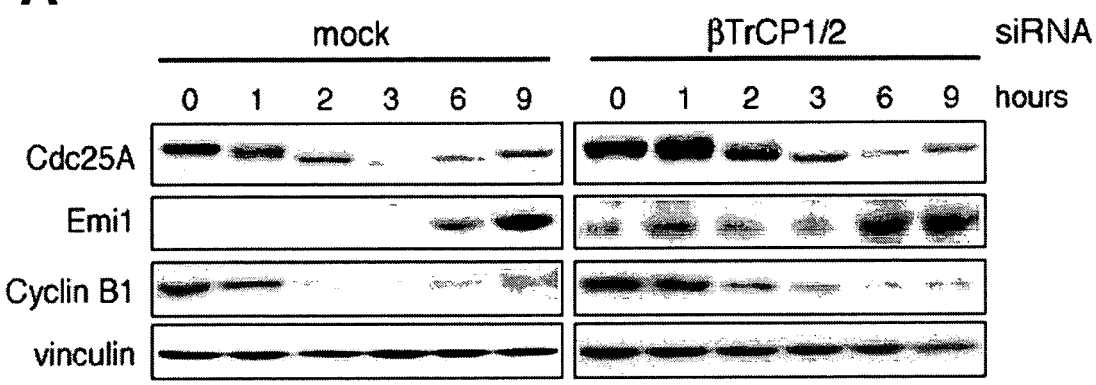
B
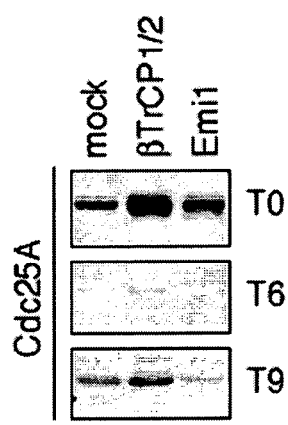
Fig. 13

US 7,439,032 B2

METHODS TO IDENTIFY COMPOUNDS USEFUL FOR TUMOR SENSITIZATION TO DNA DAMAGE

This application claims priority under 35 U.S.C. §119(e) to U.S. provisional patent application Ser. No. 60/513,525 filed on Oct. 21, 2003, the contents of which are hereby incorporated by reference in their entirety.

This invention was made with government support under grant number R01-GM57587, awarded by the National Institute of Health/General Medical Sciences. Accordingly, the United States Government has certain rights in the invention.

FIELD OF THE INVENTION

The present invention relates to methods and compositions useful for identifying candidate compounds for sensitizing a cancer cell or a tumor to DNA damage, and methods of applying such compounds for improving a cancer treatment regimen based on a DNA damaging agent. Specifically, the present invention relates to the identification and use of compounds that inhibit the expression or function of β-transducin repeat containing proteins 1 and/or 2 (hereinafter referred to as "β-TrCP1/2").

BACKGROUND OF THE INVENTION

The cell division cycle is one of the most fundamental processes in biology which, in multicellular organisms, ensures the controlled generation of cells with specialized functions. Under normal growth conditions, cell proliferation is tightly regulated in response to diverse intra- and extracellular signals. The Cdc25A phosphatase plays a critical role in cell cycle progression due to its function in dephosphorylating cyclin-dependent kinases, thus serving as a rate-limiting mitotic activator. Conversely, in response to DNA damage or stalled replication, the ATM (ataxia-telangiectasia-mutated) and ATR (ATM and Rad3-related) protein kinases activate the checkpoint kinases (Chk1 and Chk2) leading to Cdc25A hyperphosphorylation (Falck et al., Nature. 2001;410:842-7; Zhao et al., Proc Natl Acad Sci USA, 2002;24:24; Sorensen et al., Cancer Cell, 2003;3:247-58). These events stimulate the ubiquitin-mediated proteolysis of Cdc25A (Falck (2001) supra; Mailand et al., Science, 2000;288:1425-9; and Molinari et al., EMBO Rep, 2000;1:71-9) and contribute to delaying cell cycle progression, thereby preventing genomic instability (Falck (2001), supra; Zhao, supra; Sorensen, supra; Mailand, supra; Molinari, supra; Bartek & Lukas, Curr Opin Cell Biol, 2001;13:738-47; and Falck et al., Nat Genet, 2002; 30:290-4). Dysregulation of Cdc25A has also been associated with certain types of breast cancer (Cangi et al., J Clin Invest, 2000;106:753-61).

The proteolysis of cellular regulatory proteins such as Cdc25A is a multistep process orchestrated by the concerted action of three enzymes, all leading up to the addition of a ubiquitin peptide to the protein, and subsequent transfer of the ubiquitinylated protein to a cellular structure called the proteasome where it is proteolyzed. The enzymes responsible for recruitment of each particular type of target protein to be proteolyzed are called ubiquitin ligases. Given the diversity of target proteins, there is an equally large number of ubiquitin ligases. One type is called the SCF ubiquitin ligases. The SCF ubiquitin ligases comprise three subunits; a Skp1 protein, a Cul1 protein, and an F-box protein. For a review, see Pagano and Benmaamar, Cancer Cell 2003;4:1-6. Many F-box proteins have been identified and characterized (see, e.g., WO 00/12679 by Chiaur et al., and WO 02/055665 by Pagano et al.), which is often the SCF subunit responsible for targeting the target protein to be proteolyzed.

It has previously been shown that the ubiquitin-mediated degradation of Cdc25A at the exit of mitosis is mediated by the APC/C$^{Cdh1}$ (Anaphase Promoting Complex/Cyclosome) ubiquitin ligase through recognition of a specific KEN box sequence (Donzelli et al., Embo J, 2002;21:4875-84). In the same study, it was also demonstrated that a Cdc25A KEN mutant is resistant to APC-mediated ubiquitylation, yet it remains short lived in interphase cells as the wild-type protein, and it is still degraded in response to ionizing radiation, thus suggesting that Cdc25A may be targeted for degradation by a dual mechanism. Furthermore, Cdc25A degradation both in cycling cells and in response to DNA damage depends on phosphorylation events (Falck (2001), supra; Zhao, supra; Sorensen, supra; and Mailand, supra), a requirement for efficient target recruitment to SCF (Skp1/Cullin/F-box) ubiquitin ligases by F-box proteins (Jackson & Eldridge, Mol Cell, 2002;9:923-5; Patton et al., Trends Genet, 1998;14:236-43) as reported for other cell cycle regulators (reviewed in Spruck et al., Cell Cycle, 2002;1:250-4). Interestingly, a gain of function mutation in a C. elegans cdc25 gene has been described to result in a deregulated hyperproliferation of intestinal cells (Clucas, C., et al., EMBO J.,2002;21:665-74). The encoded mutated protein carries a Ser-to-Phe substitution within a putative DSG consensus.

However, despite these advances in the art, the F-box protein specifically responsible for targeting Cdc25A to degradation, has not been identified. Since Cdc25A is a key component in stalling the cell cycle in response to DNA damage, identification of the specific F-box protein can yield important tools in regulating Cdc25A and thereby the cell cycle, as well as the cellular response to DNA damage. This invention addresses these and other needs in the art.

SUMMARY OF THE INVENTION

The present invention provides methods of and kits for screening for agents useful for sensitizing a cancer cell to DNA damage by a second agent, as well as methods of treating cancer using such agents.

Accordingly, the invention provides method of screening for an agent useful for sensitizing a cancer cell to DNA damage by a second agent, which comprises: (i) contacting a β-transducin repeat containing protein (β-TrCP) with a test compound and a phosphorylated cell division cycle 25A (Cdc25A) protein or a fragment thereof; and (ii) detecting a reduced binding of the β-TrCP to the phosphorylated Cdc25A protein or fragment thereof in the presence of the test compound as compared to a control. The β-TrCP can comprise the sequence of, e.g., SEQ ID NO:3 or SEQ ID NO:6. The Cdc25A protein or fragment thereof preferably comprises the sequence of SEQ ID NO:29 or SEQ ID NO:8. The control may be the binding of the β-TrCP to the Cdc25A protein or fragment thereof in the absence of the test compound. The second agent can be, for example, ionizing radiation or an alkylating agent. In one embodiment, the β-TrCP and Cdc25A protein or fragment thereof are expressed by a cell, and the test compound is added to the cell. The cell can further express, for example, Skp1 and Cul1. In yet another embodiment, the β-TrCP, test compound, and phosphorylated Cdc25A protein or fragment are in a reconstituted system. The reconstituted system may further comprise Skp1 and Cul1.

The invention also provides a method of screening for an agent useful in sensitizing a cancer cell to DNA damage by a second agent which comprises: (i) contacting a β-TrCP with a test compound and a phosphorylated Cdc25A protein or a fragment thereof, and (ii) detecting a reduced ubiquitin ligation of the phosphorylated Cdc25A protein or fragment thereof in the presence of the test compound as compared to a control. In different embodiments, the β-TrCP comprises the sequence of SEQ ID NO:3 or SEQ ID NO:6. Preferably, he Cdc25A protein or fragment thereof comprises the sequence of SEQ ID NO:29 or SEQ ID NO:8. The control may be, for example, the ubiquitin ligation of the phosphorylated Cdc25A protein or fragment thereof in the absence of the test compound. In one embodiment, the β-TrCP and Cdc25A protein or fragment thereof are expressed by a cell, and the test compound is added to the cell. In another embodiment, the β-TrCP, test compound, and phosphorylated Cdc25A protein or fragment thereof are in a reconstituted system.

The invention also provides a method of screening for an agent useful in sensitizing a cancer cell to DNA damage by a second agent which comprises: (i) contacting a cell expressing a β-TrCP with a test compound, a phosphorylated β-TrCP substrate and a ubiquitin compound; and (ii) detecting a conformational change in the β-TrCP or a reduction in ubiquitination of the β-TrCP substrate as compared to a control. The control may be, for example, the conformation or ubiquitination in the absence of the test compound. The substrate is preferably a member of the group consisting of Cdc25A, β-catenin, Emi1, and IκB.

The invention also provides a method of treating cancer, comprising administering a β-TrCP inhibitor and a DNA damaging agent to a subject suffering from cancer, wherein the β-TrCP inhibitor sensitizes tumor cells in the patient to DNA damage. In one embodiment, the β-TrCP inhibitor reduces Cdc25A degradation. For example, the β-TrCP inhibitor can be an anti-sense or siRNA polynucleotide. In such an embodiment, the anti-sense or siRNA may comprise the sequence of a member of the group consisting of SEQ ID NO:23-SEQ ID NO:26. Exemplary DNA damaging agents are ionizing radiation or alkylating agents.

The invention also provides a method of reducing Cdc25A degradation in a cell, comprising reducing β-TrCP activity in the cell. In one embodiment, this method comprises reducing the amount of β-TrCP1, β-TrCP2, or both, in the cell by, for example, reducing the amount of β-TrCP1 mRNA, β-TrCP2 mRNA, or both. In another embodiment, the method comprises administering an anti-sense polynucleotide or siRNA to β-TrCP1, β-TrCP2, or both. In yet another embodiment, the method comprises adding an inhibitor of β-TrCP1 activity, β-TrCP2 activity, or both, to the cell.

The invention also provides a method of screening for an agent useful for sensitizing a cancer cell to DNA damage by a second agent, which comprises: (i) contacting a β-transducin repeat containing protein (β-TrCP) with a test compound and a phosphorylated cell division cycle 25A (Cdc25A) protein or a fragment thereof; (ii) comparing the binding of the β-TrCP to the phosphorylated Cdc25A protein or fragment thereof to a control; and (iii) selecting any test compound reducing the binding as a compound useful for sensitizing a cancer cell to DNA damage. In one embodiment, the β-TrCP comprises the sequence of SEQ ID NO:3 or SEQ ID NO:6. The control can be, for example, the binding of the β-TrCP to the Cdc25A protein or fragment thereof in the absence of the test compound.

The invention also provides a method of screening for an agent useful for sensitizing a cancer cell to DNA damage by a second agent which comprises: (i) contacting a β-TrCP with a test compound and a phosphorylated Cdc25A protein or a fragment thereof; (ii) comparing the ubiquitin ligation of the phosphorylated Cdc25A protein or fragment thereof as compared to a control; and (iii) selecting any test compound reducing the ubiquitin ligation as useful for sensitizing a cancer cell. In one embodiment, the β-TrCP comprises the sequence of SEQ ID NO:3 or SEQ ID NO:6. The control can be, for example, the binding of the β-TrCP to the Cdc25A protein or fragment thereof in the absence of the test compound.

The invention also provides a method of screening for an agent useful for sensitizing a cancer cell to DNA damage by a second agent which comprises: (i) contacting a cell expressing a β-TrCP with a test compound, a phosphorylated β-TrCP substrate and a ubiquitin compound; and (ii) comparing the conformation of the β-TrCP or ubiquitination of the β-TrCP substrate to a control; and (iii) selecting any test compound changing the conformation of β-TrCP or reducing the ubiquitination as useful for sensitizing a cancer cell. The β-TrCP can comprise the sequence of SEQ ID NO:3 or SEQ ID NO:6. An exemplary control is the β-TrCP conformation or the β-TrCP substrate ubiquination in the absence of the test compound.

The invention also provides a method of screening for an agent useful for sensitizing a cancer cell to DNA damage by a second agent which comprises: (i) contacting a cell expressing a β-TrCP with a test compound; and (ii) comparing the degradation rate of the β-TrCP to a control; and (iii) selecting any test compound increasing the degradation rate of β-TrCP as useful for sensitizing a cancer cell. In one embodiment, the β-TrCP comprises the sequence of SEQ ID NO:3 or SEQ ID NO:6. The control can be, for example, the degradation rate of β-TrCP in the absence of the test compound.

The invention also provides a method of screening for an agent useful in sensitizing a cancer cell to DNA damage by a second agent which comprises: (i) contacting a cell expressing β-TrCP and Cdc25A with a test compound; (ii) comparing the amount of β-TrCP or Cdc25A in the cell in the presence and absence of the test compound; and (iii) selecting any test compound decreasing the amount of β-TrCP or increasing the amount of Cdc25A as useful for sensitizing a cancer cell. The β-TrCP can comprise the sequence of, for example, SEQ ID NO:3 or SEQ ID NO:6, and an exemplary test compound is an siRNA.

The invention also provides a kit for screening for an agent useful for sensitizing a cancer cell to DNA damage by a second agent, which comprises a β-TrCP, Cdc25A protein, means for detecting binding between the β-TrCP and the Cdc25A protein, and instructions for use, as well as a kit for screening for an agent useful for reducing Cdc25A degradation, which comprises a β-TrCP, Cdc25A protein, means for detecting binding between the β-TrCP and the Cdc25A protein, and instructions for use.

These and other features of the invention are further described below.

1. WCE=whole cell extract. Asterisk indicates the position of IgG heavy chain (β-TrCP2 protein overlaps with IgG).

Figure 3:

FIG. 3. Cdc25A interacts with beta-TrCP1 and beta-TrCP2 in vivo (III). Cdc25A bound to β-TrCP proteins is phosphorylated. Immunocomplexes obtained from β-TrCP1 immunoprecipitation were treated with λ-phosphatase and analyzed for Cdc25A.

FIG. 4. Interaction with β-TrCP protein through a phosphorylated DSG motif is required for Cdc25A degradation and polyubiquitylation (I). Alignment of DSG motifs identified in known β-TrCP substrates. Serine to Alanine substitution mutants in the DSG motif of Cdc25A are indicated in the rectangle.

Figure 5:
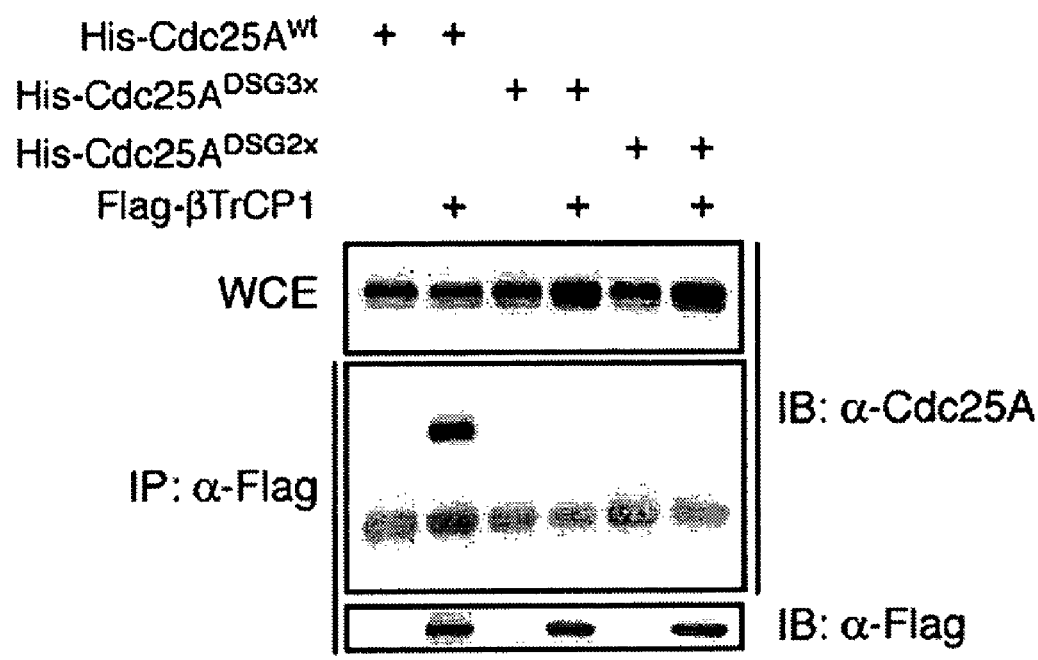

FIG. 5. Interaction with β-TrCP protein through a phosphorylated DSG motif . . . (II). His-tagged Cdc25A$^{DSG2x}$ and Cdc25A$^{DSG3X}$ constructs were co-expressed with Flag-beta-TrCP1 in HeLa cells. anti-Flag β-TrCP1 immunocomplexes were blotted for Cdc25A.

Figure 6:
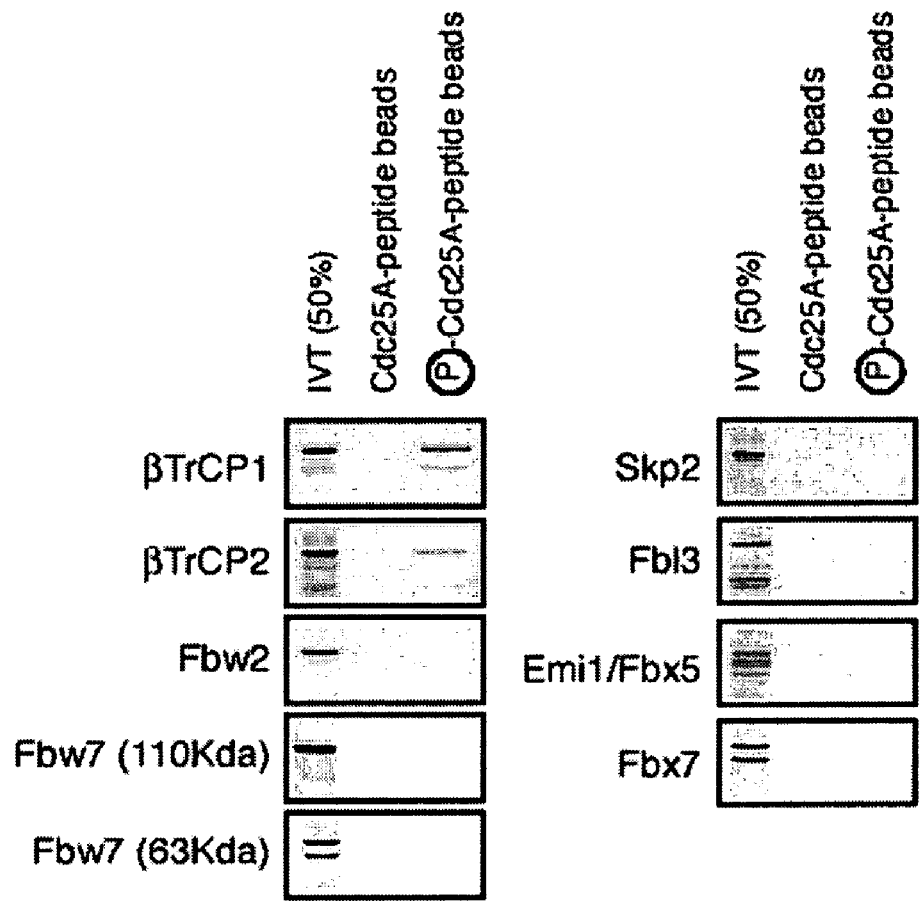

FIG. 6. Interaction with β-TrCP protein through a phosphorylated DSG motif . . . (III). Immobilized Cdc25A-derived peptides with or without phosphorylated Ser82 and Ser88 residues (panel a) were incubated with $^{35}$S-methionine-labeled in vitro-translated (IVT) F-box proteins and analyzed by autoradiography.

Figure 7:
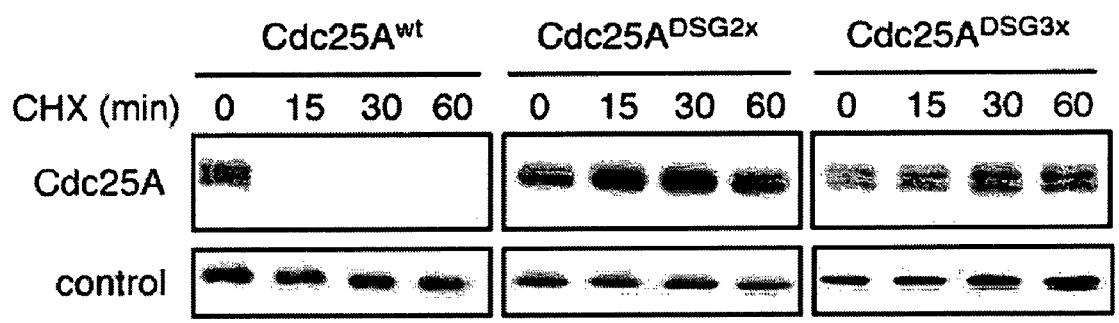

FIG. 7. Interaction with β-TrCP protein through a phosphorylated DSG motif . . . (IV). HeLa cells were transfected with the indicated Flag-tagged constructs and analyzed for Cdc25A expression upon cycloheximide treatment.

Figure 8:
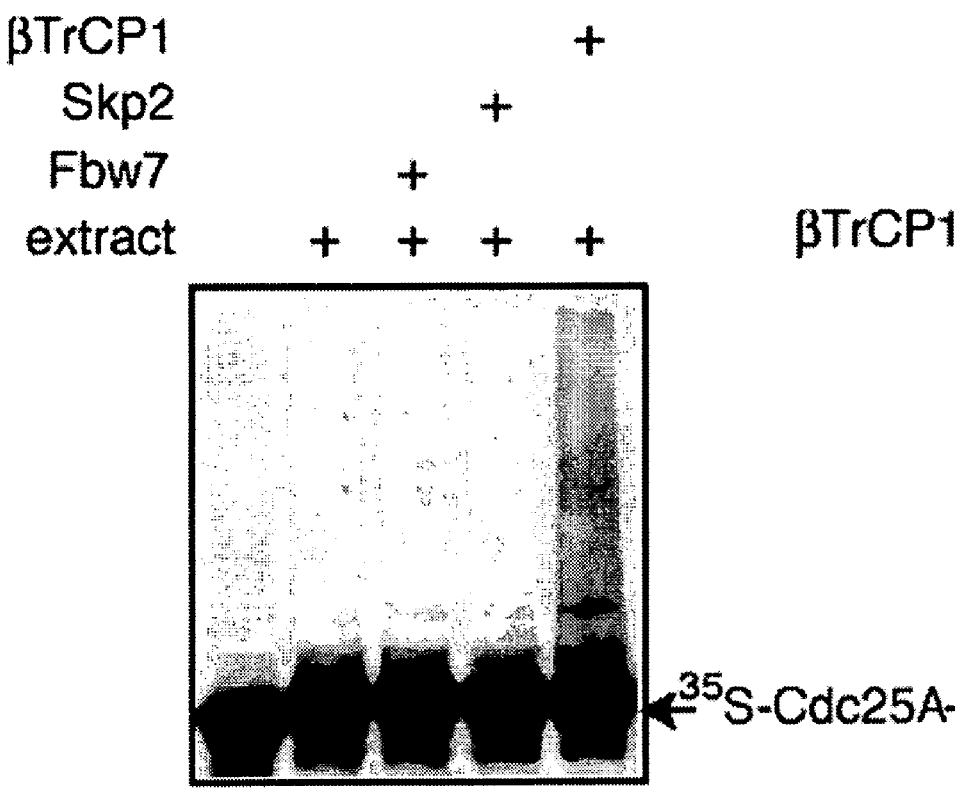

FIG. 8. Interaction with β-TrCP protein through a phosphorylated DSG motif . . . (V). $^{35}$S-methionine-labeled in vitro-translated Cdc25A was incubated with HeLa cell extract enriched with the indicated Skp1/F-box protein complexes and analyzed by autoradiography.

Figure 9:
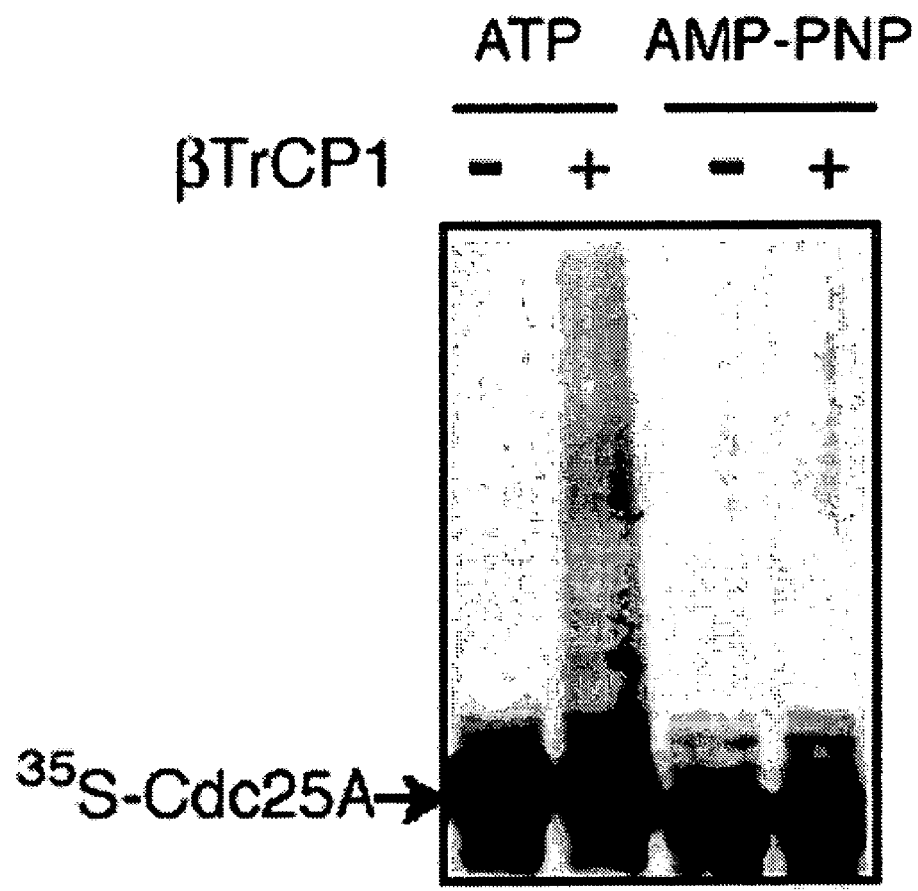

FIG. 9. Interaction with β-TrCP protein through a phosphorylated DSG motif . . . (VI). An ATP (adenosine-triphosphate) analogue, AMP-PNP (5'-adenylyl-β,γ-imido-diphosphate) was used in the ubiquitin ligation reaction.

Figure 10:
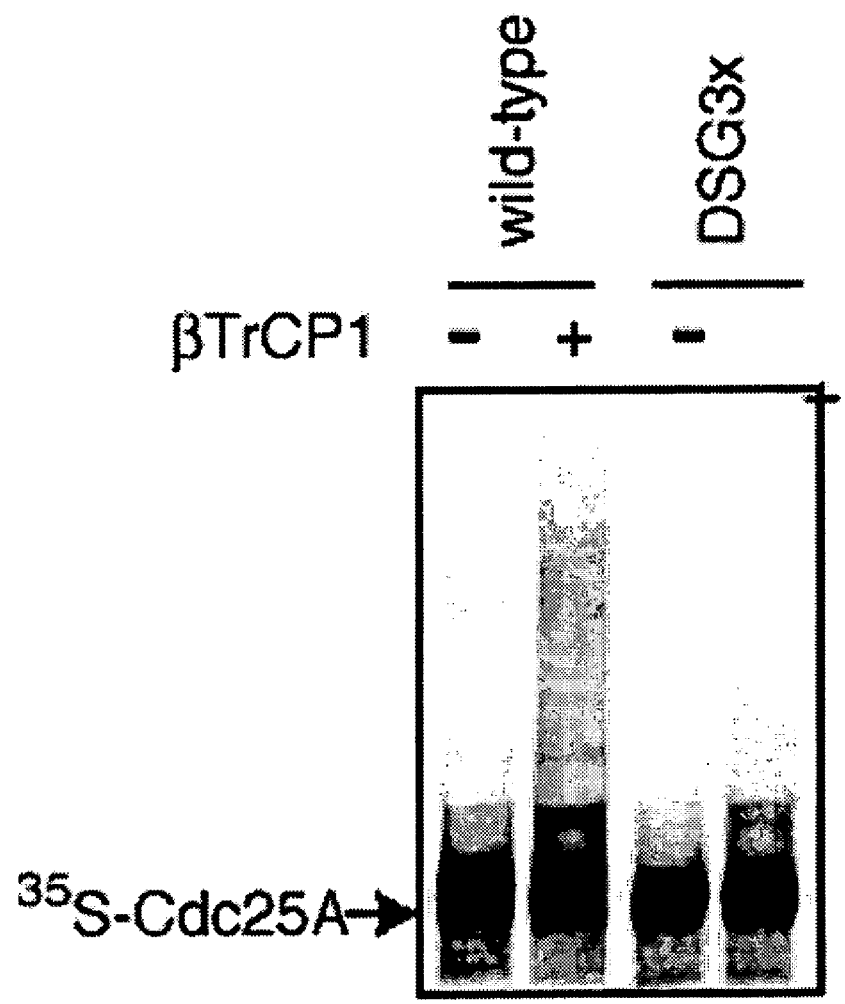

FIG. 10. Interaction with β-TrCP protein through a phosphorylated DSG motif . . . (VII). β-TrCP-mediated ubiquitylation of Cdc25$^{wt}$ and Cdc25A$^{DSG3X}$ proteins.

Figure 11:
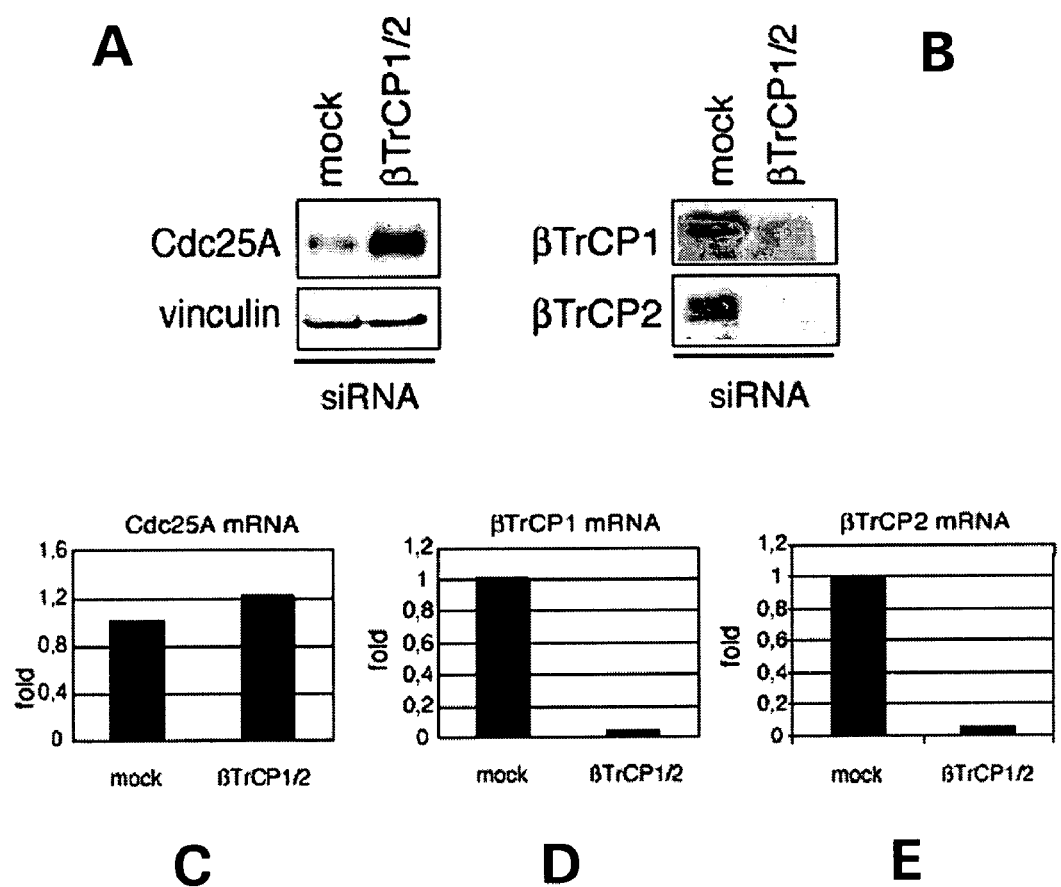

FIG. 11. β-TRCP controls Cdc25A abundance during S-phase progression (I). HeLa cells were transfected with mock or β-TrCP1/2 siRNA oligonucleotides. Cdc25A, β-TrCP1 and β-TrCP2 expression levels (immunoblotting and Q-PCR) are shown.

FIG. 12. β-TrCP controls Cdc25A abundance during S-phase progression (II). Mock, β-TrCP or Emi1 siRNA-transfected cells were synchronized by double thymidine block and released in nocodazole-containing medium. Cells were harvested at the indicated time points, lysated and blotted for Cdc25A, Emi1 and Cyclin A. Samples collected at T0, T6 (6 hours) and T12 (12 hours) time points were aligned for direct comparison of Cdc25A expression.

FIGS. 13A and B. β-TrCP controls Cdc25A abundance during S-phase progression (III). Mock, β-TrCP or Emi1 siRNA-transfected cells were synchronized by nocodazole treatment and release in drug-free medium. Cells were harvested at the indicated time points, lysed and blotted for Cdc25A, Emi1 and Cyclin B1. Samples collected at T0, T6 and T9 time points were compared for Cdc25A expression.

Figure 14:
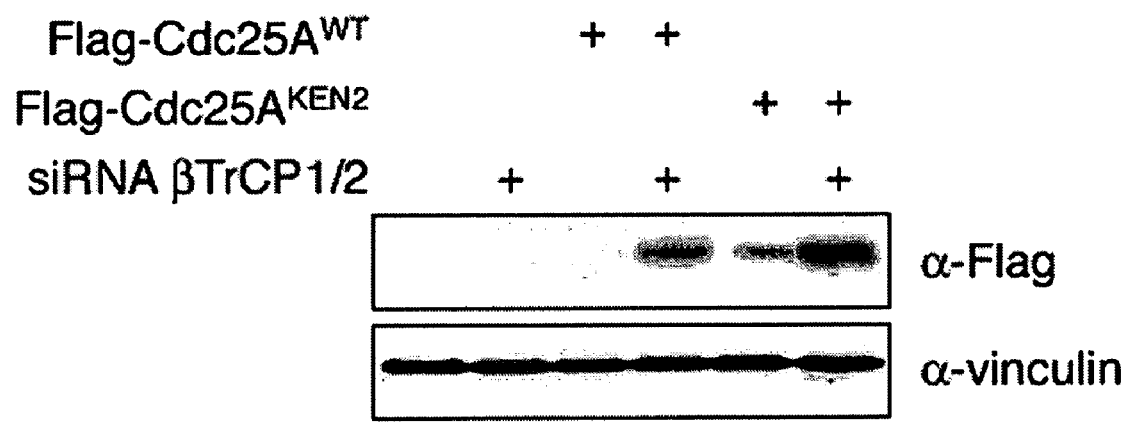

FIG. 14. β-TrCP controls Cdc25A abundance during S-phase progression (IV). Interfered cells were transfected with Flag-tagged wild-type or KEN2 mutant Cdc25A constructs and analyzed for Cdc25A overexpression.

Figure 15:
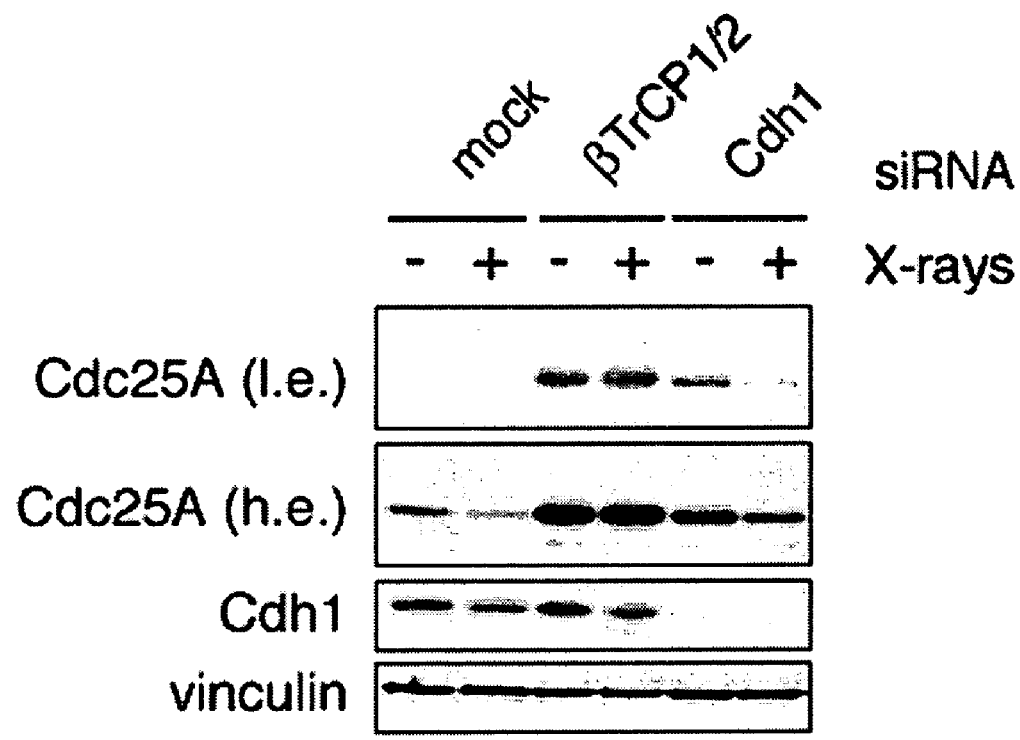

FIG. 15. β-TrCP is required for ionizing radiation (IR)-induced degradation of Cdc25A in the intra-S-phase checkpoint (I). HeLa cells were mock, β-TrCP or Cdh1 siRNA-transfected and 48 h later exposed to IR (10 Gy). Cdc25A protein levels are shown in low and high exposures.

Figure 16:
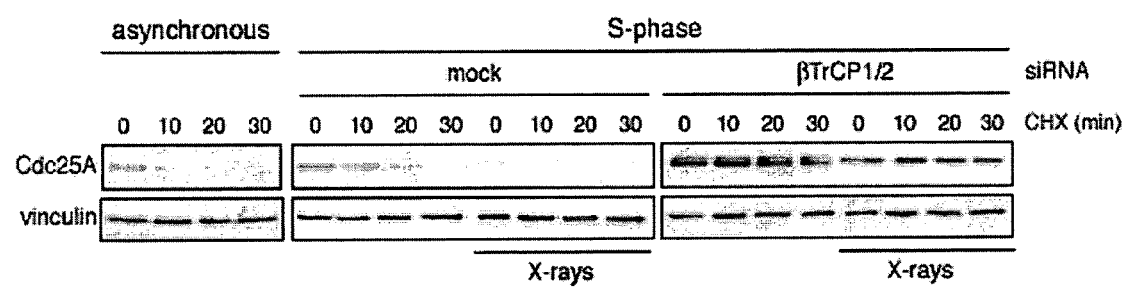

FIG. 16. β-TrCP is required for IR-induced degradation . . . (II). siRNA-transfected S-phase cells were exposed to IR and Cdc25A half-life analyzed by CHX (cycloheximide) treatment.

Figure 17:
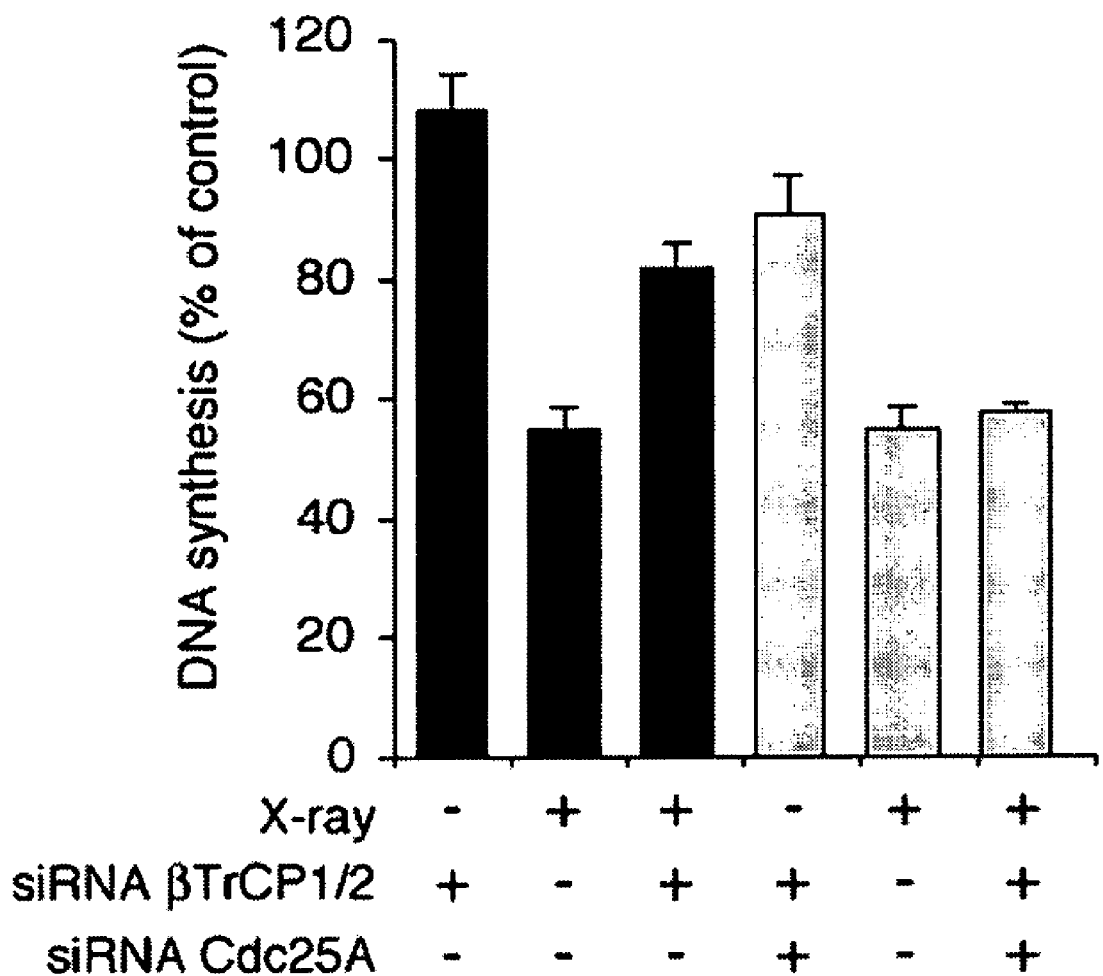

FIG. 17. β-TrCP is required for IR-induced degradation . . . (III). The percentage of DNA synthesis, normalized against mock-transfected non-irradiated cells was assessed in mock, β-TrCP1/2 or βTrCP1/2 plus Cdc25A siRNA-transfected cells, 90 min after ionizing radiation treatment.

Figure 18:
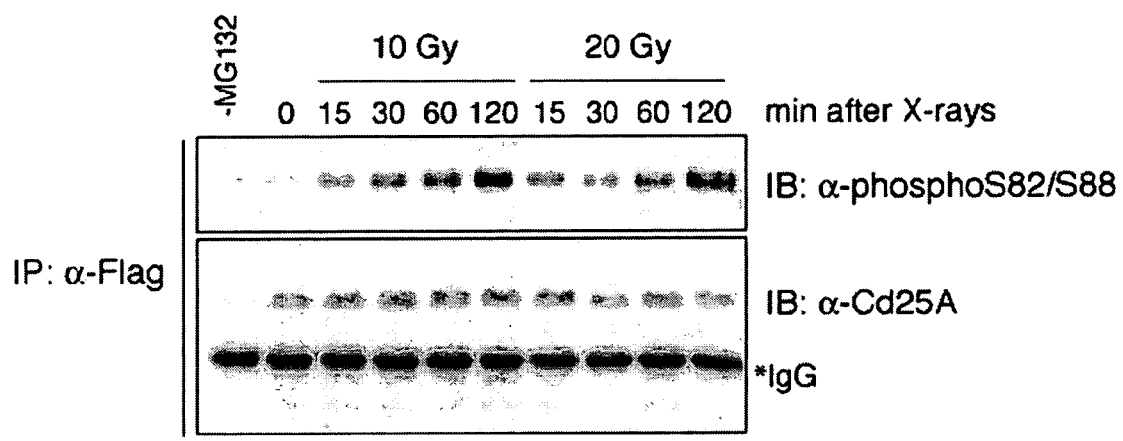

FIG. 18. β-TrCP is required for IR-induced degradation . . . (IV). HeLa cells overexpressing Flag-Cdc25A were irradiated with two IR doses (10 and 20 Gy) in the presence of the proteasome inhibitor MG132 (Biomol) and collected at the indicated time points after IR. Immunoprecipitated Cdc25A was blotted with a purified anti-phosphoS82/S88 antibody.

Figure 19:
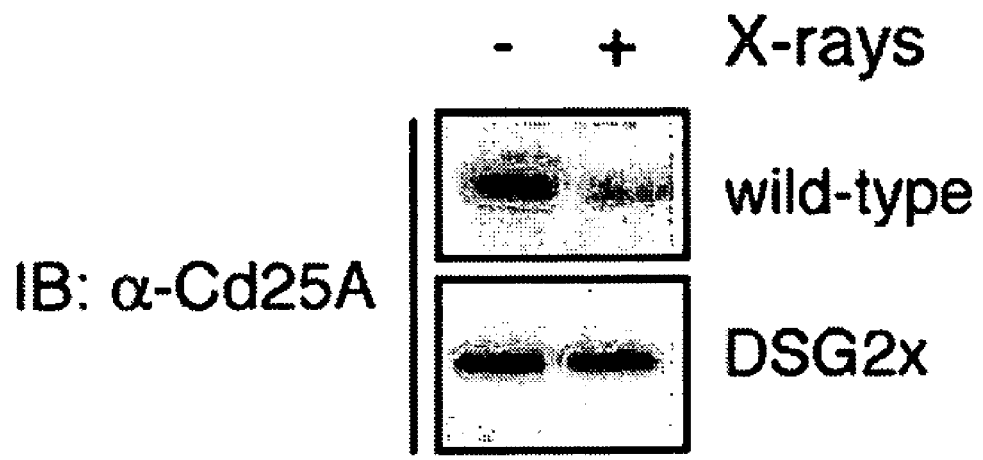

FIG. 19. U2OS cells stably expressing wild type or DSG2x proteins were mock- or IR-treated.

Figure 20:
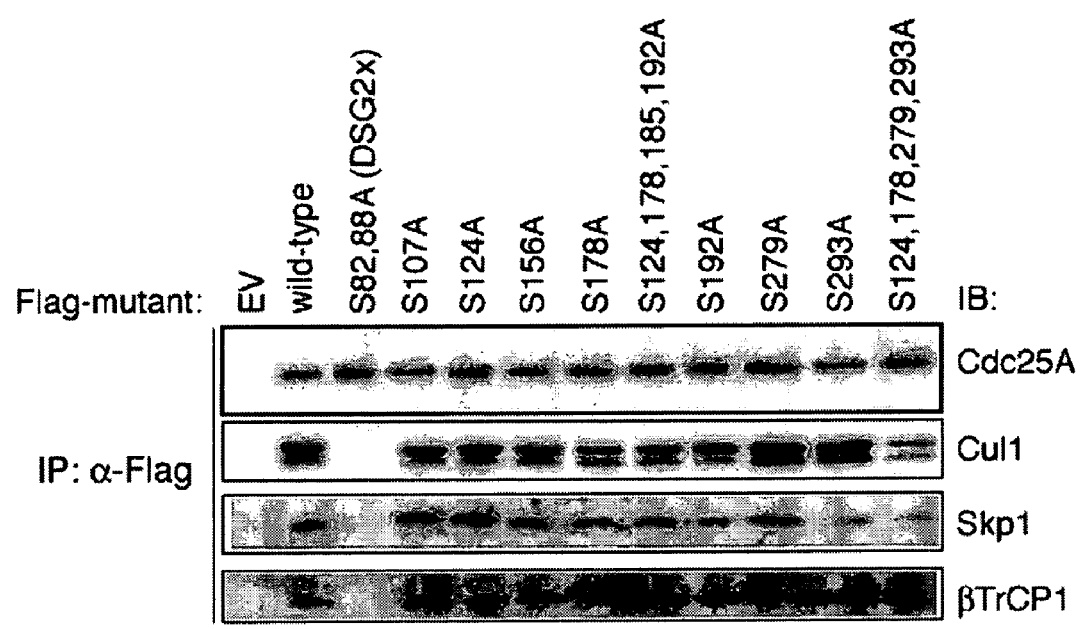

FIG. 20. Flag-tagged Cdc25A immunocomplexes were blotted for Cdc25A, Cul1, Skp1 and β-TrCP1.

DETAILED DESCRIPTION OF THE INVENTION

The present invention is based, in part, on the identification of β-TrCP as the F-box protein that targets phosphorylated Cdc25A to degradation by the SCF (Skp1/Cul1/F-box protein) complex. Accordingly, if the DNA in a cell is damaged in the absence of β-TrCP1/2 activity, or reduced activity of β-TrCP1/2, Cdc25A accumulates in a cell, upon which the cell may not hold off on proliferation to give its DNA-repairing systems time to repair the DNA damage. Proceeding with proliferation without repairing DNA damage can lead to cell death.

As shown in Example 1, β-TrCP interacts directly with phosphorylated or hyperphosphorylated Cdc25A. Example 2 locates the interaction to phosphorylated serine residues in the DSG motif of Cdc25A. Example 3 demonstrates that down-regulation of β-TrCP1 and β-TrCP2 expression by small interfering RNA (siRNA) leads to Cdc25A accumulation in cells progressing through S phase and prevents ionizing radiation-induced Cdc25A degradation. While not being bound to any specific theory, this suggests that β-TrCP may function in the intra-S-phase checkpoint. Consistent with these results, in Example 4, suppression of β-TrCP expression leads to in radioresistant DNA synthesis after DNA damage, a phenotype indicative of a defective intra-S-phase checkpoint, which is associated with the inability to regulate Cdc25A properly. These results highlight a crucial role for β-TrCP in mediating the cellular response to DNA damage through Cdc25A degradation.

Accordingly, the present invention provides for both in vitro and in vivo methods to interfere with Cdc25A degradation. For example, compounds reducing or inhibiting the expression, translation, or function or β-TrCP1 and/or β-TrCP2 such as, e.g., siRNA oligonucleotides of β-TrCP1/2, or compounds increasing the degradation of β-TrCP1/2, can sensitize cancer cells to DNA damage by ionizing radiation, alkylating agents, or other cytotoxic regimens or drugs. In vitro and in vivo methods of screening for such compounds are provided herein, as tools for identifying potential tumor sensitizers, or compounds that modulate the cell cycle or proliferation or eukaryotic cells, including mammalian cells. The methods can be based either on β-TrCP1/2 interaction with human wild-type Cdc25A (SEQ ID NO:8), as well as with fragments of Cdc25A comprising at least one, preferably two, more preferably three, and most preferably all of serine residues 76, 77, 79, 82, and 88. Exemplary fragments correspond to, e.g., residues 73-95 (SEQ ID NO:16) or residues 80-93 (SEQ ID NO:29). These embodiments are described in more detail below.

The accompanying sequence listing includes the following information for β-TrCP1, β-TrCP2, and Cdc25A: β-TrCP1 coding region (SEQ ID NO:1), β-TrCP1 cDNA (SEQ ID NO:2), β-TrCP1 protein sequence (SEQ ID NO:3), β-TrCP2 coding region (SEQ ID NO:4), β-TrCP2 cDNA (SEQ ID NO:5), β-TrCP2 protein sequence (SEQ ID NO:6), Cdc25A cDNA (SEQ ID NO:7), and Cdc25A protein sequence (SEQ ID NO:8).

DEFINITIONS

The following definitions are provided for clarity and illustrative purposes only, and are not intended to limit the scope of the invention.

A "β-transducin repeat containing protein" or "β-TrCP" herein is a protein belonging to the family of F-box proteins containing 6-7 repeats of WD40 domains. Synonyms of β-TrCP1/2 include Fbw1a, FWD1a, Fbw1b, FWD1b, FBP1, and Hos. An F-box motif is a stretch of about 40 amino acids identified as being necessary for the interaction of F-box proteins with Skp1. The consensus sequence of an F-box motif is described in Bai et al., Cell, 1996;86:263-274, hereby incorporated by reference in its entirety. A WD40 domain is a consensus sequence of about 40 amino acid repeats rich in tryptophan (Trp) and aspartic acid (Asp) residues (Neer et al., Nature, 1996;371:297-300 and references therein, all of which hereby incorporated by reference in their entireties). A β-TrCP is characterized by being capable of a substrate specificity for at least one, preferably at least two, more preferably at least three, and most preferably at least all of phosphorylated Cdc25A, β-catenin, Emi1 (Guardavaccaro et al., Developmental Cell, 2003;4:799-812), and IkB (Soldatenkov et al., Cancer Res, 1999;59:5085-5088). A β-TrCP preferably has at least 50%, 70%, 80%, 90%, 95%, 96%, 97% 98%, or 99% sequence identity to at least one of the β-TrCP1 amino acid sequence (SEQ ID NO:3) and the β-TrCP2 amino acid sequence (SEQ ID NO:6), and includes functionally equivalent derivates of β-TrCP1 and β-TrCP2 such as mutants, conjugates (including radiolabeled or chemically tagged β-TrCP1/2), fusion proteins, and fragments thereof, which retain the substrate specificity of a β-TrCP. "β-TrCP1/2" means "β-TrCP1 and/or β-TrCP2".

As used herein, a "β-TrCP inhibitor" is a compound or agent reducing β-TrCP1/2 expression, translation, or activity, or increasing β-TrCP1/2 degradation.

A "cell division cycle 25A" or "Cdc25A" protein herein means a protein comprising a peptide sequence corresponding at least to residues 82-88 of human wild-type Cdc25A (SEQ ID NO:8). Preferably, the peptide sequence comprises the sequence of SEQ ID NO:29, corresponding to residues 80-93 of human wild-type Cdc25A. To function as a substrate for a β-TrCP, the serine residues corresponding to residues 82 and 88 of SEQ ID NO:8 must be at least phosphorylated, preferably double phosphorylated. Exemplary Cdc25A fragments useful for testing binding to or ubiquitination by β-TrCP1/2 include peptides corresponding to residues 73-95 (SEQ ID NO:16) and residues 80-93 (SEQ ID NO:29).

A "DNA damaging agent" is a chemical compound or treatment method that induces DNA damage when applied to a cell, including single-strand breaks, double-strand breaks and alkylation. Such agents include, without limitation, ionizing radiation and waves that induce DNA damage, such as γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Contemplated chemotherapeutic agents include alkylating agents such as mitomycin C, adozelesin, cis-platinum, and nitrogen mustard.

"Ubiquitin ligation", "ubiquitination", and "ubiquitinylation" as used herein all refer to the addition of a ubiquitin polypeptide to a protein substrate targeted for degradation. The Skp1/Cul1/F-box (SCF) ubiquitin ligase unit is one of many ubiquitin ligases capable of catalyzing a ubiquitin ligation reaction. The F-box protein β-TrCP is one of many F-box proteins specifically recruiting substrates for ubiquitin ligation. Among the substrates for β-TrCP are β-catenin, Emi1, IkB, and, as described in the Examples, Cdc25A. Ubiquitination of a substrate is believed to take place on one or more lysine residues, and can be detected by assays described herein (see, e.g., the Examples) and in, e.g., Carrano et al. (Nat Cell Biol 1, 193-199 (1999)).

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

MOLECULAR BIOLOGY—DEFINITIONS

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition, Cold Spring Harbor, N.Y., Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis, M. J. Gait (Ed.) (1984); Nucleic Acid Hybridization, B. D. Hames & S. J. Higgins eds. (1985); Transcription And Translation, B. D. Hames & S. J. Higgins, eds. (1984); Animal Cell Culture, R. I. Freshney, ed. (1986); Immobilized Cells And Enzymes (IRL Press, (1986)); B. Perbal, A Practical Guide To Molecular Cloning (1984); Ausubel, F. M. et al. (eds.), and Current Protocols in Molecular Biology, John Wiley & Sons, Inc., 1994.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides" in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thiouracil, thioguanine and fluorouracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"Amplification" of DNA as used herein denotes the use of polymerase chain reaction (PCR) to increase the concentration of a particular DNA sequence within a mixture of DNA sequences. For a description of PCR see Saiki et al., Science, 1988, 239:487.

"Chemical sequencing" of DNA denotes methods such as that of Maxam and Gilbert (Maxam and Gilbert, Proc. Natl. Acad. Sci. USA, 1977; 74:560 et seq., in which DNA is randomly cleaved using individual base-specific reactions.

"Enzymatic sequencing" of DNA denotes methods such as that of Sanger (Sanger et al., Proc. Natl. Acad. Sci. USA, 1977;74:5463 et seq., in which a single-stranded DNA is copied and randomly terminated using DNA polymerase, including variations thereof well-known in the art.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981, 290:304 310), the promoter contained in the 3' long terminal repeat of Rous sarcoma virus (Yamamoto et al., Cell, 1980, 22:787 797), the herpes thymidine kinase promoter (Wagner et al., Proc. Natl. Acad. Sci. USA, 1981;78:1441-1445), the regulatory sequences of the metallothionein gene (Brinster et al., Nature, 1982;296:39-42); prokaryotic expression vectors such as the beta lactamase promoter (Villa Komaroff et al., Proc. Natl. Acad. Sci. USA, 1978;75:3727 3731), or the tac promoter (DeBoer et al., Proc. Natl. Acad. Sci. USA, 1983;80:21-25); see also "Useful proteins from recombinant bacteria" in Scientific American, 1980;242:74 94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta globin gene control region which is active in myeloid cells (Mogram et al., Nature, 1985;315:338-340; Kollias et al., Cell, 1986;46:89-94), hematopoietic stem cell differentiation factor promoters, erythropoietin receptor promoter (Maouche et al., Blood, 1991;15:2557), etc.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" transcriptional and translational control sequences in a cell when RNA polymerase transcribes the coding sequence into RNA, particularly mRNA, which is then trans-RNA spliced (if it contains introns) and translated into the protein encoded by the coding sequence.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wisc.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a genetic machinery of a cell. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described infra.

The term "expression system" means a host cell and compatible vector under suitable conditions, e.g. for the expression of a protein coded for by foreign DNA carried by the vector and introduced to the host cell. Common expression systems include $E.\ coli$ host cells and plasmid vectors, insect host cells and Baculovirus vectors, and mammalian host cells and vectors. In a specific embodiment, the protein of interest is expressed in COS-1 or C2C12 cells. Other suitable cells include CHO cells, HeLa cells, 293T (human kidney cells), mouse primary myoblasts, and NIH 3T3 cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed, e.g., a CHO cell.

The terms "mutant" and "mutation" mean any detectable change in genetic material such as DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

"Sequence conservative variants" of a polynucleotide sequence are those in which a change of one or more nucleotides in a given codon position results in no alteration in the amino acid encoded at that position.

"Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell, 1987;50:667). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90 or 95%, 96%, 97%, 98%, or 99% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90%, 91%, 92%, 93%, 94%, 95%, 96%, 97%, 98%, or 99% are similar (functionally identical) or identical. Preferably, the similar or homologous sequences are identified by alignment using, for example, the GCG (Genetics Computer Group, Program Manual for the GCG Package, Version 7, Madison, Wisc.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

An "antisense nucleic acid" is a single stranded nucleic acid molecule which, on hybridizing under cytoplasmic conditions with complementary bases in an RNA or DNA molecule of interest, inhibits the expression of the latter. If the RNA is a messenger RNA transcript, the antisense nucleic acid is a counter-transcript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids encoding the protein. In a further embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific non limiting examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. No. 5,792,844 and U.S. Pat. No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza-nitrogen atoms of the polyamide backbone (Nielsen et al., Science, 1991;254:1497 et seq.). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$ ; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Expression of β-TrCP1/2 Polypeptides and β-TrCP1/2 Substrates

For the screening and evaluation of compounds for their ability to modulate the β-TrCP1/2 interaction with Cdc25A or other β-TrCP substrates, both in vitro (including reconstituted systems) and in vivo systems (including cellular systems and transgenic animals) systems can be used. Regardless of the screening or testing system of choice, various expression methods can be employed to provide the protein components or cellular/transgenic animals to be used in the method.

A wide variety of host/expression vector combinations (i.e., expression systems) may be employed in expressing DNA sequences for β-TrCP1 or fragments or mutants thereof, β-TrCP2 or fragments or mutants thereof, Cdc25A or fragments or mutants thereof, Skp1, Cul1, β-catenin, Emi1, IκB-α, IκB-β, IκB-ε, and other components to be included. These may be co-expressed from the same vector, expressed from different vectors, or one may be expressed while the other one is added externally to the screening or evaluation system. Useful expression vectors, for example, may consist of segments of chromosomal, non chromosomal and synthetic DNA sequences. Suitable vectors include derivatives of SV40 and known bacterial plasmids, e.g., E. coli plasmids col E1, pCR1, pBR322, pMa1-C2, pET, pGEX (Smith et al., Gene, 1988;67:31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, various tumor cells lines can be used in expression systems of the invention.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, Bam-HI, SacI, KpnI, and HindIII cloning site, N-terminal peptide purified with ProBond resin and cleaved with enterokinase; Invitrogen), to mention just two, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and U.S. Pat. No. 5,168,062), the SV40 early promoter region (Benoist and Chambon, Nature, 1981;290:304-310), the promoter contained in the 3' long terminal repeat of Rous sarcoma virus (Yamamoto, et al., Cell, 1980;22:787-797), the herpes thymidine kinase promoter (Wagner et al., Proc. Natl. Acad. Sci. U.S.A., 1981;78:1441-1445), the regulatory sequences of the metallothionein gene (Brinster et al., Nature, 1982;296:39 42); prokaryotic expression vectors such as the β-lactamase promoter (Villa-Komaroff, et al., Proc. Natl. Acad. Sci. U.S.A., 1978;75:3727-3731), or the tac promoter (DeBoer, et al., Proc. Natl. Acad. Sci. U.S.A., 1983;80:21-25); see also "Useful proteins from recombinant bacteria" in Scientific American, 1980;242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature, 1985;315:338-340; Kollias et al., Cell, 1986;46:89-94), hematopoietic stem cell differentiation factor promoters, erythropoietin receptor promoter (Maouche et al., Blood, 1991;15:2557), etc.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992;7:980-990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991; 2:320-330), defective herpes virus vector lacking a glycoprotein L gene (Patent Publication RD 371005 A), or other defective herpes virus vectors (International Patent Publication No. WO 94/21807, published Sept. 29, 1994; International Patent Publication No. WO 92/05263, published Apr. 2, 1994); an attenuated adenovirus vector, such as the vector described by Stratford-Perricaudet et al. (J. Clin. Invest., 1992;90:626-630; see also La Salle et al., Science, 1993;259: 988-990); and a defective adeno-associated virus vector (Samulski et al., J. Virol., 1987;61:3096-3101; Samulski et al., J. Virol., 1989;63:3822-3828; Lebkowski et al., Mol. Cell. Biol., 1988;8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine 1995). In that regard, it is advantageous to employ a viral vector that is engineered to express a minimal number of antigens.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem., 1992;267:963-967; Wu and Wu, J. Biol. Chem., 1988;263:14621-14624; Hartmut et al., Canadian Patent Application No. 2,012,311, filed Mar. 15, 1990; Williams et al., Proc. Natl. Acad. Sci. USA, 1991;88:2726-2730). Receptor-mediated DNA delivery approaches can also be used (Curiel et al., Hum. Gene Ther., 1992;3:147-154; Wu and Wu, J. Biol. Chem., 1987;262:4429-4432). U.S. Pat. Nos. 5,580,859 and 5,589,466 disclose delivery of exogenous DNA sequences, free of transfection facilitating agents, in a mammal. A relatively low voltage, high efficiency in vivo DNA transfer technique, termed electrotransfer, has also been described (Mir et al., C.P. Acad. Sci., 1998;321:893; WO 99/01157; WO 99/01158; WO 99/01175).

Another option is to transcribe and translate cDNA sequences in vitro. Various commercial systems are available for such techniques, including the TNT Quick Coupled Transcription/Translation System with Transcend™ (Promega, Madison, Wisc.). For in vitro production of labeled or modified peptides or proteins, labeled or chemically modified amino acid precursors such as, e.g., $^{35}$S-methionine or phosphoserine, can be added to the translation system.

Transgenic Animals

Transgenic mammals can be prepared for evaluating the interaction of human β-TrCP1/2 and Cdc25A or any other β-TrCP1/2 substrates. Such mammals provide excellent models for screening or testing drug candidates, i.e., β-TrCP inhibitors. Thus, human β-TrCP1/2 "knock-in" mammals can be prepared for evaluating the molecular biology of this system in greater detail than is possible with human subjects. In one embodiment, the animal can be double-transgenic, in that both human β-TrCP1/2 and human Cdc25A is expressed in the transgenic animal. It is also possible to evaluate compounds or diseases in "knock-out" animals, e.g., to identify a compound that can compensate for a defect in β-TrCP1/2 and/or Cdc25A. Both technologies permit manipulation of single units of genetic information in their natural position in a cell genome and to examine the results of that manipulation in the background of a terminally differentiated organism. Trangenic mammals can be prepared by any method, including but not limited to modification of embryonic stem (ES) cells and heteronuclear injection into blast cells.

A "knock-in" mammal is a mammal in which an endogenous gene is substituted with a heterologous gene (Roemer et al., New Biol., 1991;3:331). Preferably, the heterologous gene is "knocked-in" to a locus of interest, either the subject of evaluation (in which case the gene may be a reporter gene; see Elefanty et al., Proc Natl Acad Sci USA, 1998;95:11897) of expression or function of a homologous gene, thereby linking the heterologous gene expression to transcription from the appropriate promoter. This can be achieved by homologous recombination, transposon (Westphal and Leder, Curr Biol, 1997;7:530), using mutant recombination sites (Araki et al., Nucleic Acids Res, 1997;25:868) or PCR (Zhang and Henderson, Biotechniques, 1998;25:784).

A "knock-out mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 1995;9:2623 34) describes PPCA knock out mice. The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. Generally, for homologous recombination, the DNA will be at least about 1 kilobase (kb) in length and preferably 3-4 kb in length, thereby providing sufficient complementary sequence for recombination when the knockout construct is introduced into the genomic DNA of the ES cell. Double knock-out mammals can be generated by repeating the procedures set forth herein for generating each knock-in or knock-out construct, or by breeding to mammals, each with a single gene knocked out, to each other, and screening for those with the double knockout genotype. Regulated knockout animals can be prepared using various systems, such as the tet-repressor system (see U.S. Pat. No. 5,654,168) or the Cre-Lox system (see U.S. Pat. No. 4,959,317 and U.S. Pat. No. 5,801,030). The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

In another series of embodiments, transgenic animals are created in which (i) a human β-TrCP1/2 and/or Cdc25A is stably inserted into the genome of the transgenic animal; and/or (ii) the corresponding endogenous genes are inactivated and replaced with their human counterparts (see, e.g., Coffman, Semin. Nephrol., 1997;17:404; Esther et al., Lab. Invest., 1996;74:953; Murakami et al., Blood Press. Suppl., 1996;2:36). Such animals can be treated with candidate compounds and monitored for neuronal development, neurodegeneration, or efficacy of a candidate therapeutic compound.

Antibodies to β-TrCP1/2 and β-TrCP1/2 Substrates

As described in the Examples, various antibodies useful for detecting β-TrCP1/2 or their substrates, including Cdc25A, have been produced, some of which are available commercially. Such antibodies may be used in immunoblotting or immunoprecipitation techniques to study binding of β-TrCP1/2 to one of its substrates, to detect ubiquitinated Cdc25A, to inhibit interaction between β-TrCP1/2 and Cdc25A or one of its other substrates, or for other purposes in the screening and treatment methods described herein. Additional antibodies with different specificity or other particular properties may also be prepared. Antibodies useful for these purposes include but are not limited to polyclonal, monoclonal, chimeric, single chain, Fab fragments, and Fab expression library.

Various procedures known in the art may be used for the production of polyclonal antibodies. For example, various host animals can be immunized by injection with the antigenic polypeptide, including but not limited to rabbits, mice, rats, sheep, goats, etc. For preparation of monoclonal antibodies, any technique that provides for the production of antibody molecules by continuous cell lines in culture may be used. These include but are not limited to the hybridoma technique originally developed by Kohler and Milstein (Nature, 1975;256:495-497), as well as the trioma technique, the human B-cell hybridoma technique (Kozbor et al., Immunology Today, 1983;4:72, Cote et al., Proc. Natl. Acad. Sci. U.S.A., 1983;80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec. 1989).

According to the invention, techniques described for the production of single chain antibodies (U.S. Pat. Nos. 5,476,786 and 5,132,405 to Huston; U.S. Pat. No. 4,946,778) can be adapted to produce polypeptide-specific single chain antibodies. Indeed, these genes can be delivered for expression in vivo to, e.g., express an antibody inhibiting β-TrCP1/2 interaction with Cdc25A. An additional embodiment of the invention utilizes the techniques described for the construction of Fab expression libraries (Huse et al., Science, 1989;246:1275-1281) to allow rapid and easy identification of monoclonal Fab fragments with the desired specificity for a PTPN11 polypeptide, or its derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Screening

A "test substance" or "test compound" is a chemically defined compound or mixture of compounds (as in the case of a natural extract or tissue culture supernatant), whose ability to modulate β-TrCP1/2 activity may be defined by various assays. A "test substance" is also referred to as a "candidate drug" or "candidate compound" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wisc.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech, 1996;14:60).

A modulatory effect may be determined by an in vitro method using a recombinant β-TrCP1/2-reporter gene promoter activity system. Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, in particular reduced or eliminated, the test substance has modulated, e.g., inhibited, β-TrCP1/2-mediated gene expression, and is thus a candidate for development of Cdc25A modulator tumor sensitizing agent. The reporter gene assay system described here may be used in a high-throughput primary screen for antagonists, or it may be used as a secondary functional screen for candidate compounds identified by a different primary screen, e.g., a binding assay screen that identifies compounds that modulate β-TrCP1/2 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing genes encoding at least one of β-TrCP1/2 and Cdc25A, optionally also the remaining components of an SCF complex, can be used in screening methods to identify candidate drugs. In one series of embodiments, a permanent cell line is established. Alternatively, cells are transiently programmed to express a β-TrCP1/2 gene by introduction of appropriate DNA or mRNA. As described herein, transgenic animals can also be used to screen for or study β-TrCP1/2 inhibitors.

Identification of candidate substances can be achieved using any suitable assay, including without limitation (i) assays that measure selective binding of test compounds to β-TrCP1/2, Cdc25A, or another one of its substrates (ii) assays that measure the ability of a test substance to modify (e.g., inhibit) a measurable activity or function of β-TrCP1/2 or Cdc25A, (iii) assays that measure the ability of a substance to modify (i.e., inhibit) the transcriptional activity of sequences derived from the promoter (i.e., regulatory) regions of the β-TrCP1/2 gene; and (iv) assays that modulate (e.g., promote) the degradation of β-TrCP1/2 proteins.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

β-TrCP1/2 Binding to Cdc25A

One type of assay useful for screening for inhibitors of β-TrCP1/2 activity with regards to Cdc25A is based on detection of β-TrCP1/2 binding to its Cdc25A substrate. Such assays may be based on either β-TrCP1/2 binding to full-length Cdc25A or fragments thereof. These assays may be based on full-length Cdc25A or fragments of the same, corresponding to, e.g., SEQ ID NO:16 or SEQ ID NO:29 of human Cdc25A, either in vitro translated, synthesized, or prepared from a fragmented full-length Cdc25A protein. Preferably, one or more of the serine residues are phosphorylated or double phosphorylated in advance, or a phosphorylation agent is added to phosphorylate the Cdc25A to the desired degree.

In one embodiment, the Cdc25A protein or peptides can be coupled to agarose beads or another solid-phase system. The coupled protein or peptides can then be contacted with β-TrCP1 and/or β-TrCP2, and the effect of an added test compound on the binding of the β-TrCP1/2 to the Cdc25A protein or peptide can be evaluated. For example, the β-TrCP1/2 can be radiolabeled or chemically tagged, or an anti-β-TrCP1/2 antibody can be used to detect whether or not the β-TrCP1/2 is bound to the solid phase in the presence of the test compound. A lack of binding in the presence of compound is indicative of a β-TrCP1/2 inhibitor.

β-TrCP1/2 Activity Assays

A screening assay can also be based on the detection of β-TrCP1/2 activity in the presence or absence or a test compound. For example, the ubiquitination of a β-TrCP1/2 substrate, preferably Cdc25A, by an SCF-complex comprising β-TrCP1/2 can be detected by various means, including immunoassays, gel electrophoresis, and the like.

In one embodiment, Cdc25A is incubated at 30° C. in a ubiquitinylation mix containing, for example, 40 mM Tris pH 7.6, 5 mM $MgCl_2$, 1 mM DTT, 10% glycerol, 1 μM ubiquitin aldehyde, 1 mg/ml methyl ubiquitin, 10 mM creatine phosphate, 0.1 mg/ml creatine kinase, 0.5 mM ATP, 1 μM okadaic acid, and 20 µg cell extract obtained from prometaphase MEFs using a "cell nitrogen-disruption bomb" (Parr, cat #4639). Purified and/or recombinant SCF complexes are then added, and the reaction stopped after an appropriate time period. Ubiquitinylated Cdc25A can then be detected by, e.g., labeling of ubiquitin or the Cdc25A itself, in combination with a chomatographic method, gel electrophoresis method, or by using an antibody specific for ubiquitinylated Cdc25A.

The assays can also be conducted in a cellular system. For example, a test compound can added to a cell culture to test whether its presence induces the accumulation of β-TrCP1/2 substrates (i.e., Cdc25A, β-catenin, Emi1, and IκB), modifies ubiquitination of β-TrCP1/2 substrates, and/or stabilizes Cdc25A in response to DNA damage. After an appropriate period of incubation with the test compound, the cells are collected and lysed. One or more β-TrCP1/2 substrates are then immunoprecipitated with specific antibodies against β-TrCP1/2 substrates (see Examples) and immunoblotted with an antibody against ubiquitin (see, e.g., Bloom et al., Cell, 2003;115:71-82). The amounts of β-TrCP1/2 substrates, ubiquitinated β-TrCP1/2 substrates, and/or Cdc25A are then compared to controls (e.g., cell cultures not incubated with test compound).

Many suitable methods for evaluation and detection of Cdc25A can also be found in U.S. Pat. No. 6,322,975 to Beach et al., hereby incorporated by reference in its entirety.

Therapeutic Use

According to the present invention, β-TrCP1/2 inhibitors can be used to sensitize the cancer cells in a cancer patient to DNA damage by a second agent. The second agent can be, for example, ionizing radiation, or an alkylating agent such as mitomycin C, adozelesin, cis-platinum, or nitrogen mustard. The β-TrCP1/2 inhibitor can, for example, be included in a regular treatment regimen based on radiation therapy or chemotherapy so that the β-TrCP1/2 inhibitor is administered before, after, or in conjunction with the DNA damaging agent. Generally, the treatment regimen is optimized to maximize DNA damaging effect of tumor cells while minimizing side effects on normal tissues and discomfort for the patient. The method comprises administering to a patient in need of such treatment an effective amount of an agent that modulates β-TrCP1/2 expression, activity, or binding to Cdc25A, with a pharmaceutically acceptable carrier. For example, the therapeutic agent may be a β-TrCP1/2 antisense nucleic acid or siRNA, or an anti-β-TrCP1/2 or anti-Cdc25A intracellular inhibitory antibody. In one embodiment, the modulatory agent may be a substance that is known or has been identified to modulate, especially inhibit, whether fully or partially, β-TrCP1/2 expression or activity. Alternatively, this modulatory agent may be a candidate drug as identified by a screening method as described above. All these embodiments are described in greater detail below.

A "subject" or "patient" is a human or an animal with, or who is likely to develop, cancer, more particularly a mammal, preferably a rodent or a primate. The term "treatment" or "therapy" means to therapeutically intervene in the development of a disease in a subject showing a symptom of this disease.

Known or candidate β-TrCP1/2 inhibitors can be evaluated for use in conjunction of radiation therapy or chemotherapy in any type of cancer, including metastatic and primary cancers, as well as cancer characterized by solid tumors or non-solid tumors such as hematologic malignancies. Examples of solid tumors include sarcomas, carcinomas, and other tumors such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas.

Inhibitory Antibodies

The modulatory substance can be an antibody that is directed against β-TrCP1/2 or Cdc25A. Antibodies that block the activity of β-TrCP1/2 or interaction between β-TrCP1/2 and Cdc25A or another substrate may be produced and selected according to any standard method well-known by one skilled in the art, such as those described above.

Intracellular antibodies (sometime referred to as "intrabodies") have been used to regulate the activity of intracellular proteins in a number of systems (see, Marasco, Gene Ther., 1997;4:11; Chen et al., Hum. Gene Ther., 1994;5:595), e.g., viral infections (Marasco et al., Hum. Gene Ther., 1998;9: 1627) and other infectious diseases (Rondon et al., Annu. Rev. Microbiol., 1997;51:257), and oncogenes, such as p21 (Cardinale et al., FEBS Lett., 1998; 439:197-202; Cochet et al., Cancer Res., 1998;58:1170-6), myb (Kasono et al., Biochem Biophys Res Commun., 1998;251:124-30), erbB-2 (Graus-Porta et al., Mol Cell Biol., 1995;15:1182-91), etc. This technology can be adapted to inhibit β-TrCP1/2 activity by expression of an anti-β-TrCP1/2 intracellular antibody.

Antisense Therapy

In another embodiment, vectors comprising a sequence encoding an antisense nucleic acid according to the invention may be administered by any known methods, such as the methods for gene therapy available in the art. Exemplary methods are described below. For general reviews of the methods of gene therapy, see, Goldspiel et al., Clinical Pharmacy, 1993;12:488 505; Wu and Wu, Biotherapy, 1991;3:87 95; Tolstoshev, Ann. Rev. Pharmacol. Toxicol., 1993;32:573-596; Mulligan, Science, 1993;260:926-932; and Morgan and Anderson, Ann. Rev. Biochem., 1993;62:191-217; May, TIBTECH, 1993;11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA, 1989;86:8932 8935; Zijlstra et al., Nature, 1989;342:435 438).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell surface receptors or transfecting agents, encapsulation in biopolymers (e.g., poly −.1 □4 N acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor mediated endocytosis (see, e.g., Wu and Wu, J. Biol. Chem., 1987;62:4429 4432), etc. In another embodiment, a nucleic acid ligand complex can be formed in which the ligand comprises a fusogenic viral peptide to disrupt endosomes, allowing the nucleic acid to avoid lysosomal degradation, or cationic 12 mer peptides, e.g., derived from antennapedia, that can be used to transfer therapeutic DNA into cells (Mi et al., Mol. Therapy, 2000;2:339 47). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

RNA Interference (RNAi or siRNA)

Another technique of interest for therapeutic purposes is based on the same principles employed for interfering with β-TrCP translation in a cellular system, namely siRNA technology. Particularly, expression of selected genes can be suppressed in human cells by transfecting with exogenous, short RNA duplexes (siRNA) where one strand corresponds to a target region of the mRNA, i.e., EST of interest (Elbashir et al., Nature, 2001;411:494-498). The siRNA molecules are typically greater than 19 duplex nucleotides, and upon entry into the cell, siRNA causes the degradation of single-stranded (ssRNAs) RNAs of identical sequences, including endogenous mRNAs. siRNA is more potent than standard antisense technology since it acts through a catalytic mechanism. Effective strategies to deliver siRNAs to target cells in cell culture include physical or chemical transfection. An alternative strategy uses the endogenous expression of siRNAs by various Pol III promoter expression cassettes that allow transcription of functional siRNAs or their precursors (Scherr et al., Curr. Med. Chem., 2003;10(3):245-56). Recently, the RNA-polymerase III dependent promoter (H1-RNA promoter) was inserted in the lentiviral genome to drive the expression of a small hairpin RNA (shRNA) against enhanced green fluorescent protein (Abbas-Turki et al., Hum. Gene Ther., 2002;13(18):2197-201). siRNA can also be delivered in a viral vector derived, e.g., from a lentivirus (Tiscornia et al., Proc. Natl. Acad. Sci. U.S.A., 2003;100: 1844-8). For review articles, see Hannon, Nature, 2002;418: 244-51 and Bernstein et al., RNA, 2001;7(11):1509-21. This technology also has been described in vitro in cultured mammalian neurons in Krickevsky and Kosik, Proc. Natl. Acad. Sci. USA, 2002;99(18):11926-9. siRNA technology is also being used to make transgenic animals (Cornell et al., Nat. Struct. Biol., 2003;10(2):91-2). RNA is described in Publication Nos. WO 99/49029 and WO 01/70949.

Exemplary siRNA duplexes suitable for β-Trcp1 silencing can be based on 21 bp synthetic molecules (Dharmacon Research) corresponding to nucleotides 195-213 (CCC AGG GAC UGG CGC ACU CdTdT (SEQ ID NO:23)) and nucleotides 1082-1100 (UUC UCA CAG GCC AUA CAG GdTdT (SEQ ID NO:24)) of the human β-Trcp1 coding region (NM_033637; SEQ ID NO:1). For β-Trcp2 silencing, an oligo corresponding to nucleotides 183-203 (GAG GCC AUC AGA AGG AAA CdTdT (SEQ ID NO:25)) of the human β-Trcp2 coding region (AB033279; SEQ ID NO:4) can be used used. An siRNA oligo corresponding to both nucleotides 515-535 of human β-Trcp1 and 262-282 of human β-Trcp2 (GUG GAA UUU GUG GAA CAU CdTdT (SEQ ID NO:26)) can also be used. For interfering with translation of β-TrCP1/2 substrates, cdh1 gene siRNA can be based on oligos corresponding to the nucleotide sequence 5'-AATGAGAAGTCTCCCAGTCAG (SEQ ID NO: 27) and 5'-AATCTGGTGGACTGGTCGTCC-3' (SEQ ID NO:28), Emi1 siRNA duplexes corresponding to nucleotides 567-589 can be used, and for Cdc25A siRNA duplexes corresponding to nucleotides 82-102 of human Cdc25A can be used.

Formulations and Administration

When formulated in a pharmaceutical composition, a therapeutic compound such as a β-TrCP1/2 inhibitor can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and, more particularly, in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "therapeutically effective amount" is used herein to mean an amount or dose sufficient to modulate, e.g., decrease the level of β-TrCP1/2 activity e.g., by about 10 percent, preferably by about 50 percent, and more preferably by about 90 percent. Preferably, a therapeutically effective amount is sufficient to cause an improvement in a clinically significant condition in the host following a therapeutic regimen involving one or more β-TrCP1/2 inhibitors. The concentration or amount of the active ingredient depends on the desired dosage and administration regimen, as discussed below. Suitable dosages may range from about 0.01 mg/kg to about 100 mg/kg of body weight per day, week, or month. The pharmaceutical compositions may also include other biologically active compounds.

According to the invention, a therapeutically effective amount of the β-TrCP1/2 inhibitor can be formulated in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Optionally, the β-TrCP1/2 inhibitor can be formulated together with an DNA damaging agent such as an alkylating agent.

In another embodiment, the active ingredient can be delivered in a vesicle, in particular a liposome (see Langer, Science, 1990;249:1527-1533; Treat et al., in Liposomes in the Therapy of Infectious Disease and Cancer, Lopez-Berestein and Fidler (eds.), Liss: NewYork, pp. 353-365 (1989); Lopez-Berestein, ibid., pp. 317-327; see generally ibid.).

In yet another embodiment, the therapeutic compound(s) can be delivered in a controlled release system. For example, a polypeptide may be administered using intravenous infusion with a continuous pump, in a polymer matrix such as poly-lactic/glutamic acid (PLGA), a pellet containing a mixture of cholesterol and the active ingredient (SilasticRTM; Dow Coming, Midland, Mich.; see U.S. Pat. No. 5,554,601) implanted subcutaneously, an implantable osmotic pump, a transdermal patch, liposomes, or other modes of administration.

EXAMPLES

The present invention is further described by means of the example, presented below. The use of such an example is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Materials & Methods

The following describes the materials and methods employed in Examples 1-4.

Cells. HeLa (human carcinoma; obtained from ATCC) or U2OS (human osteosarcoma) cells are used in the Examples. Cell culture is conducted essentially as described in Donzelli et al. (Embo J, 2002;21:4875-84). Cells are grown at 37° C. in a 5% CO2 atmosphere in Dulbecco's modified Eagle's medium (Euroclone) supplemented with 10% bovine calf serum (Hyclone) and 2 mM L-glutamine (Euroclone), or in DMEM containing 5% FCS.

Cell Synchronizations. This is conducted essentially as described in Donzelli et al. (2002), supra. Briefly, to obtain HeLa cells arrested at specific stages of the cell cycle, nocodazole treatment is used. Cells are synchronized in metaphase by treatment with 0.05 µg/ml nocodazole for 16 h. Rounded cells are collected by gentle pipetting and released from drug-induced cell cycle block by washing three times with phosphate-buffered saline (PBS) and re-plated in drug-free medium. Cells are collected at different time points up to 12 h.

Cells are synchronized in early S-phase by double thymidine treatment (2 mM) for 12 h, and released in drug-free medium for 8 and 12 h. Cell cycle position can be monitored by flow cytometry. The following procedure is used: Thymidine (Sigma Chemical Co.) is prepared as a 100 mM stock solution in phosphate buffered saline, pH 7.4. Briefly, (1) exponentially growing cells are diluted to $2.5 \times 10^5$/ml with fresh medium supplemented with 2 mM thymidine for 12 hours. During this period, the G2/M cells progress into G1 and then, with the original G1 population, acquire a biochemical state equivalent to a G1/S phase border cell. (G2M=3.6 hours+G1=8.4 hours, TOTAL=12 hours). Any cells in S phase upon addition of thymidine are blocked in S phase. (2) Release of the cells from the first thymidine block is performed by centrifuging suspension cells (600×g for 5 minutes), discarding the thymidine-medium and washing twice in an equal volume of complete medium. For monolayer cultures, the thymidine is removed by pouring-off the thymidine-medium, and adding fresh medium, repeat twice for a total of three washes. (3) Cells are then incubated in fresh medium for 16 hours. During this period the cells recover from the thymidine-block (approximately 1-2 hours) and progress through the cell cycle, divide and enter G1 of the next cell cycle. Entry into G1 of the next cell will commence with the cells that were blocked at the end of S phase (the leading-edge cells). This takes about 5-6 hours following release from thymidine block (1-2 hours recovery+4 hours progression through G2/M). Entry into G1 of the next cell cycle will end with the lagging-edge cells (those arrested at G1/S) progressing through the cell cycle and dividing (between 16 and 18 hours). (4) At the end of the 16 hour release period, cells are diluted to $2.5 \times 10^5$/ml and re-incubated with 2 mM thymidine-containing medium for 12-14 hours. Cells in G2/M or G1 would progress and arrest at the G1/S phase border. Flow cytometric determination of cell cycle position at 8-10 hours following the re-addition of thymidine will ensure that the population of cells is sufficiently synchronized before the more complex cell cycle study is commenced. (5) Release of cells from the second thymidine block follows essentially the washing procedures laid out in Step 2.

Cycloheximide Treatment. To inhibit protein synthesis, cells are cultured in the presence of 10 µg/ml cycloheximide for the indicated time points. Inhibition of protein synthesis in metaphase-arrested cells is achieved as follows: cells are treated with 0.05 µg/ml nocodazole for 16 h, and rounded cells are collected by gentle pipetting and cultured further with 0.05 µg/ml nocodazole and 10 µg/ml cycloheximide for up to 120 min. Inhibition of protein synthesis in cells exiting mitosis as achieved as follows: nocodazole-arrested cells are released in drug-free medium for 1 h and cultured further with 10 µg/ml cycloheximide for up to 60 min.

$CaPO_4$ Transfection. The following protocol describes transfection in a 24-well plate. On Day 1, cells are seeded at $5 \times 10^5$ cells/well, and left in medium containing fetal calf serum (FCS). On Day 2, cells are re-feed cells with 1 ml fresh medium containing FCS. A DNA precipitate is prepared by mixing 47.5 µl 1×TBS (TBS: 8 g NaCl, 0.2 g KCl, 3 g Tris base, in 1 L, pH 7.4)] with 20 µl DNA (500 µg/ml), and 7.5 µl 2.5 M $CaCl_2$. The above mix is added to 75 µl 2×HBS (8 g NaCl, 6 g Hepes, 0.2 g $Na_2HPO_4$ (anhydrous) per 500 ml, pH 7.1, sterile-filtered) The precipitate is then added directly to the medium on cells, and the cells incubated for 3 hours at 37° C. The medium is removed, and 1 ml 15% glycerol in PBS (8 g NaCl, 0.2 g KCl, 1.44 g $Na_2HPO_4$, 0.24 g $KH_2PO_4$ in 1 L, pH 7.4, autoclaved) is added to each well. After 1 minute, the glycerol is removed, taking great care not to dislodge cells (some cell types become less well attached after glycerol shock), and the cells washed with PBS or serum free medium. One ml growth medium is added, and left at 37° C. for 6-72 hours.

Plasmids. Flag- and His-tagged Cdc25A mutants are generated using the QuickChange Site-directed Mutagenesis kit (Stratagene, La Jolla, Calif.). All constructs are verified by DNA sequencing. Flag-tagged constructs encoding full-length or truncated versions of Cdc25 A were generated as follows: the full-length cDNA for Cdc25 A was obtained as a PCR product from pRC-CMV-Cdc25 A and cloned into the EcoRV restriction site of pCDNA3.1-FlagA; the 51-CT mutant was generated by PvuII-XhoI digestion of the full-length flagged construct and the insertion of the fragment into EcoRV-XhoI-digested FlagB-plasmid; and the 170-CT was produced by BglII-XhoI digestion of the full-length flagged construct and the insertion of the fragment into BamHI-XhoI-digested FlagB-plasmid. pCDNA3.1-Flag-Cdc25 A point mutants were generated using the QuikChange Site-directed Mutagenesis kit (Stratagene). All constructs were verified by DNA sequencing.

Cell Lysis. This procedure is used to lyse cells prior to immunoblotting and immunoprecipitation. Each plate is rinsed once with cold PBS (5 ml for a 100 mm plate), and aspirated off. The plates are placed on ice and 1 ml of lysis buffer (see below) added. When lysis becomes apparent, keeping the lid on, the plate is held partially open with one hand while tilting the plate to one side. Using a pipette, aspirate and re-release buffer until the particulate cellular matter has accumulated in the pool. Collect each of the lysates into centrifuge tubes, and spin at maximum speed for 5-10 minutes at 4° C. to pellet cell debris. Add 50 to 100 µl of Protein A beads (in a 50% slurry, pre-washed with PBS) to new centrifuge tubes, transfer the cell lysate supernatants to the new tubes, and place at 4° C. for 20 to 30 minutes (pre-clearing step). Preimmune sera or normal sera may be used to further pre-clear the cell lysate as necessary. After the pre-clearing step, centrifuge the lysate in a microcentrifuge for 5 minutes at low speed (4000-5000 rpm) to pellet the beads. The supernatant is now ready for immunoprecipitation. Lysis buffer: Nonidet P-40 lysis buffer (NP-40 LB). NP-40: 50 mM Tris-HCl (pH 7.5), 150 mM NaCl, 0.5% NP-40, and 50 mM NaF). Immediately before use, add the following 100× stocks to the lysis buffer: 100 mM $NaVO_3$ in $ddH_2O$, 100 mM DTT in $ddH_2O$, 100 mM PMSF in 100% isopropyl alcohol, and 100× Protease inhibitor (2.5 mg/ml Leupeptin, 2.5 mg/ml Aprotinin, 100 mM (=15 mg/ml) Benzamidine, and 1 mg/ml Trypsin inhibitor in ddH20.

Antibodies. The following antibodies are used for immunoblotting and/or immunoprecipitation: anti-Cdc25A (F6, Santa Cruz Biotechnology, Santa Cruz, Calif.); anti-Flag (M2, Sigma); anti-Cul1 (Zymed, San Francisco, Calif.); anti-Cyclin B 1 (GNS1, Santa Cruz); anti-Cyclin A (H-432, Santa Cruz), anti-Myc (9E10, Santa Cruz); anti-vinculin (Sigma), anti-Skp1 (1C10F4, Zymed), anti-β-TrCP1 (polyclonal serum), anti-β-TrCP2 (N-15, Santa Cruz); anti-Emi1 antibody (provided by P. K. Jackson at Stanford University School of Medicine, Calif., USA); and anti-Cdh1 monoclonal antibodies (supplied by K. Helin at European Institute of Oncology, Milan, Italy).

Immunoprecipitation. Add the desired antibody or antibodies (with or without competing peptides) as appropriate to fresh 1.5 ml Eppendorf tubes. Add pre-cleared cell lysate supernatant to the appropriate tubes, not carrying over any beads, and incubate at cold temperature for 2 hours to overnight. Add pre-washed Protein A beads to each of the tubes, and place in cold for 1 hour. Spin the tubes for 2 minutes at 2000 rpm to pellet the beads. Aspirate off the supernatants. Wash the pellets with a large volume (1 ml) of lysis buffer per tube (i.e., lysis buffer without protease inhibitors). Spin the tubes for 2 minutes at 2000 rpm, and then aspirate off the supernatant as before. Repeat for a total of three washes. After the final aspiration, add 10 µl of 2×SDS sample buffer to the lid of each tube, and briefly spin the tubes to draw the sample buffer down to the pellet. Boil the samples on a 100° C. heater for 4 minutes. Load all of the supernatant onto a SDS gel and run the gel. If conducting an immuno-blotting, proceed to description below. For autoradiography, dry and develop the gel via phospho-imaging (2 hours to an overnight exposure) and/or standard autoradiography (2 to 5 day exposure while stored at −80 degrees with enhancer screens).

Western Blotting (IP-Western). Immuno-blotting is conducted essentially as described in Donzelli et al. (2002), supra. Wet three pieces of the Whatman paper in Western transfer buffer (48 mM Tris Base, 39 mM Glycine, 0.0375% SDS, and 20% Methanol in $ddH_2O$), remove excess of buffer and place them onto the platinum anode (BIO-RAD semi-dry trans-blot SD). Wet the nitrocellulose in the same buffer and place it onto the Whatman paper. Wet the gel in the transfer buffer for 5 to 10 seconds and place it onto the nitrocellulose. Wet three pieces of Whatman paper and, removing excess of buffer, place them onto the gel. Air bubbles should be removed throughout this procedure. Place the trans-blot cathode onto the stack. Transfer the gel at a constant voltage between 15 to 25V for 30 minutes.

Place the nitrocellulose in staining solution (100 ml $dH_2O$ and 1 ml Ponceau S solution (2 g Ponceau S, 30 ml trichloroacetic acid, 100 ml $dH_2O$) to stain for 2 to 5 minutes. Pour out the Ponceau S staining solution, and rinse twice with $dH_2O$. Pour out the $dH_2O$ and add some PBS to de-stain the nitrocellulose, with slow shaking until the protein bands disappear (about 5 to 10 minutes). Pour off the PBS, and add blocking solution (100 ml 1×PBS, 0.1 ml Tween-20, 5 g non-fat dry milk) to the nitrocellulose (30 to 50 ml per filter). Place the dish on a shaker (slow) for at least 1 hour to overnight. Pour out the blocking solution and rinse the blot once with PBS. Pour off the PBS, and add enough blocking solution to cover the nitrocellulose. Also add the primary antibody. The dilution of antibody used is entirely antibody dependent. The range of dilution runs from 1:5 (for some low titer monoclonal antibodies, it is possible to directly incubate the filter in the hybridoma supernatant without any dilution) to 1:5000. Place the dish on a shaker (slow) for at least 1 hour to overnight at room temperature. Transfer the blot to a new dish. Wash the blot five to six times each for 10 minutes with 0.1% Tween-20 in PBS and slow shaking. Add some blocking solution and secondary antibody (e.g. horseradish peroxidase-conjugated mouse anti-rabbit antibody in a 1:10,000 dilution if the primary antibody is of rabbit origin and the signal is to be detected by luminescence) to the nitrocellulose. Continue with slow shaking for 1 hour at room temperature. Wash the blot 5 times for 10 minutes each with 0.1% Tween-20 in PBS and slow shaking as before. Wash the blot once for 5 minutes with PBS and slow shaking.

The blot is now ready for developing with the detection reagents. Using ECL detection reagents (RPN 2106, Amersham), mix equal volumes of each of the reagents in a fresh dish. Place the blot in the mixture for exactly 1 minute, with frequent agitation, making sure all blot surfaces receive sufficient contact with the reagents. Place saran-wrapped blot in an X-ray cassette, and using a timer, expose the blot to X-ray film for between 30 seconds to 5 minutes. Develop the films, and if available time remains, adjust the exposure times as necessary.

Phosphatase treatment. 500 units of λ protein phosphatase (New England Biolabs, Beverly, Mass.) were added to beta-TrCP immunocomplexes in the presence of $MgCl_2$ for 30 min at 30° C.

Peptide binding assay. Two peptides corresponding to the amino acid sequence TDSGFCLDSPGPLD (SEQ ID NO:29) of human Cdc25A were synthesized (Eurogentec, Philadelphia, Pa.), one of which double phosphorylated on serine residues. The peptides were coupled to agarose beads using the Aminolink Kit (Pierce, Rockford, Ill.). Coupled Cdc25A peptides (10 !ig) were incubated with $^{35}$S-methionine-labeled in vitro-translated β-TrCP1 and β-TrCP2 proteins obtained using the TNT-coupled reticulocyte lysate system (Promega, Madison, Wisc.) in the presence of 5 μCi of $^{35}$S-labeled methionine (Amersham Biosciences, Piscataway, N.Y.). Agarose beads were washed with RIPA buffer and binding was assayed by SDS-PAGE followed by autoradiography.

In vitro Ubiquitination Assay. Ubiquitin ligation was determined essentially as described in Carrano et al. (Nat Cell Biol, 1999;1:193-199), using $^{35}$S-methionine-labeled in vitro-translated Cdc25A. Baculovirus β-TrCP1, Skp2 or Fbw7 were all co-expressed with $His_6$-Skp1, purified by nickel-agarose chromatography and added at roughly similar amounts to the reaction. Briefly, 2 μl of in vitro-translated $^{35}$S-labeled Cdc25A was incubated at 30° C. for various time periods in 10 μl of ubiquitinylation mix containing 40 mM Tris pH 7.6, 5 mM $MgCl_2$, 1 mM DTT, 10% glycerol, 1 μM ubiquitin aldehyde, 1 mg/ml methyl ubiquitin, 10 mM creatine phosphate, 0.1 mg/ml creatine kinase, 0.5 mM ATP, 1 μM okadaic acid, and 20 μg cell extract obtained from prometaphase MEFs using a "cell nitrogen-disruption bomb" (Parr, cat #4639). Where indicated, approximately 5 ng of purified recombinant SCF complexes were added. Reactions were stopped with Laemmli sample buffer and the products were run on protein gels under denaturing conditions. Polyubiquitinylated Cdc25A forms were identified by autoradiography. Roc1/Ha-Cul1/His-Skp1/β-Trcp1 and Roc1/Ha-Cul1/His-Skp1/Skp2 complexes were expressed in 5B insect cells and purified by Nickel-Agarose chromatography.

siRNA. Cdh1 (Donzelli et al., (2002), supra); β-TrCP1/2 (Guardavaccaro et al., In vivo Dev Cell 4, 799-812 (2003); Margottin-Goguet et al., Dev Cell, 2003;4:813-26); Emi1 (Hsu et al., Nat Cell Biol, 2002;4:358-66); and Cdc25A (Zhao et al., Proc Natl Acad Sci USA, 2002; 24:24) 21 base pairs siRNA oligonucleotides were from Dharmacon Research Inc. (Lafayette, Colo.). Cells were transfected with siRNA duplexes by Oligofectamine (Invitrogen, Carlsbad, Calif.), following manufacturer's instructions.

Briefly, the siRNA oligos used for β-Trcp1 silencing were 21 bp synthetic molecules (Dharmacon Research) corresponding to nucleotides 195-213 (oligo L, CCC AGG GAC UGG CGC ACU CdTdT (SEQ ID NO:23)) and nucleotides 1082-1100 (oligo H, UUC UCA CAG GCC AUA CAG GdTdT (SEQ ID NO:24)) of the human β-Trcp1 coding region (NM_033637). For β-Trcp2 silencing, an oligo corresponding to nucleotides 183-203 (oligo D, GAG GCC AUC AGA AGG AAA CdTdT (SEQ ID NO:25)) of the human β-Trcp2 coding region (AB033279) was used. An siRNA oligo corresponding to both nucleotides 515-535 of human β-Trcp1 and 262-282 of human β-Trcp2 (oligo 1/2, GUG GAA UUU GUG GAA CAU CdTdT (SEQ ID NO:26)) was also used. For the cdh1 gene siRNA, oligos corresponding to the nucleotide sequence 5'-AATGAGAAGTCTCCCAGT-CAG (SEQ ID NO: 27) and 5'-AATCTGGTGGACTG-GTCGTCC-3' (SEQ ID NO:28) were used. For the Emi1 oligonucleotide sequence, siRNAs duplexes corresponding to nucleotides 567-589 were used. For the Cdc25A siRNA oligonucleotide sequence, the small interfering RNA (siRNA) oligonucleotide corresponded to nucleotides 82-102 of human Cdc25A.

Radio-Resistant DNA Synthesis Assay. Cells were transfected with siRNA duplexes, and 4 h later labeled for 24 h with 20 nCi/ml [$^{14}$C]thymidine (Amersham Biosciences), followed by another 24 h incubation in non-radioactive medium. Cells were irradiated with 10 Gy, incubated for 90 min at 37° C. and in the last 20 min pulse-labeled with 5 μCi/ml [$^{3}$H]thymidine (Amersham Biosciences). The medium was then removed and cells washed twice with PBS, once with 5% trichloracetic acid (TCA), twice with 100% ethanol and then lysed with 200 μl of a 1% SDS, 10 mM NaOH buffer. 150 μl was assayed in a liquid scintillation counter. The resulting ratios of $^{3}$H counts/min to $^{14}$C counts/min represented a measure of the DNA synthesis.

Example 1

Screening for F-Box Proteins Interacting with Cdc25A

It was previously established that Cdc25A is in complex with Cul1 and Skp1 (Donzelli, M. et al., Embo J 21, 4875-84 (2002)). In this Example, the possible involvement of SCF in the degradation of Cdc25A was investigated.

A number of human F-box proteins, including β-TrCP1 (Fbw1a), β-TrCP2 (Fbw1b), Fbw2, Fbw4, Fbw5, Fbw7 (110 kD), Fbw7 (63 kD), Skp2 and Fbl3 were screened for interaction with Cdc25A (Cenciarelli et al., Curr Biol, 1999;9: 1177-9; Kipreos & Pagano, Genome Biol 1, REVIEWS3002 (2000)). As a control, we assessed that the Cul1 subunit was complexed to all the F-box proteins tested.

Figure 1:
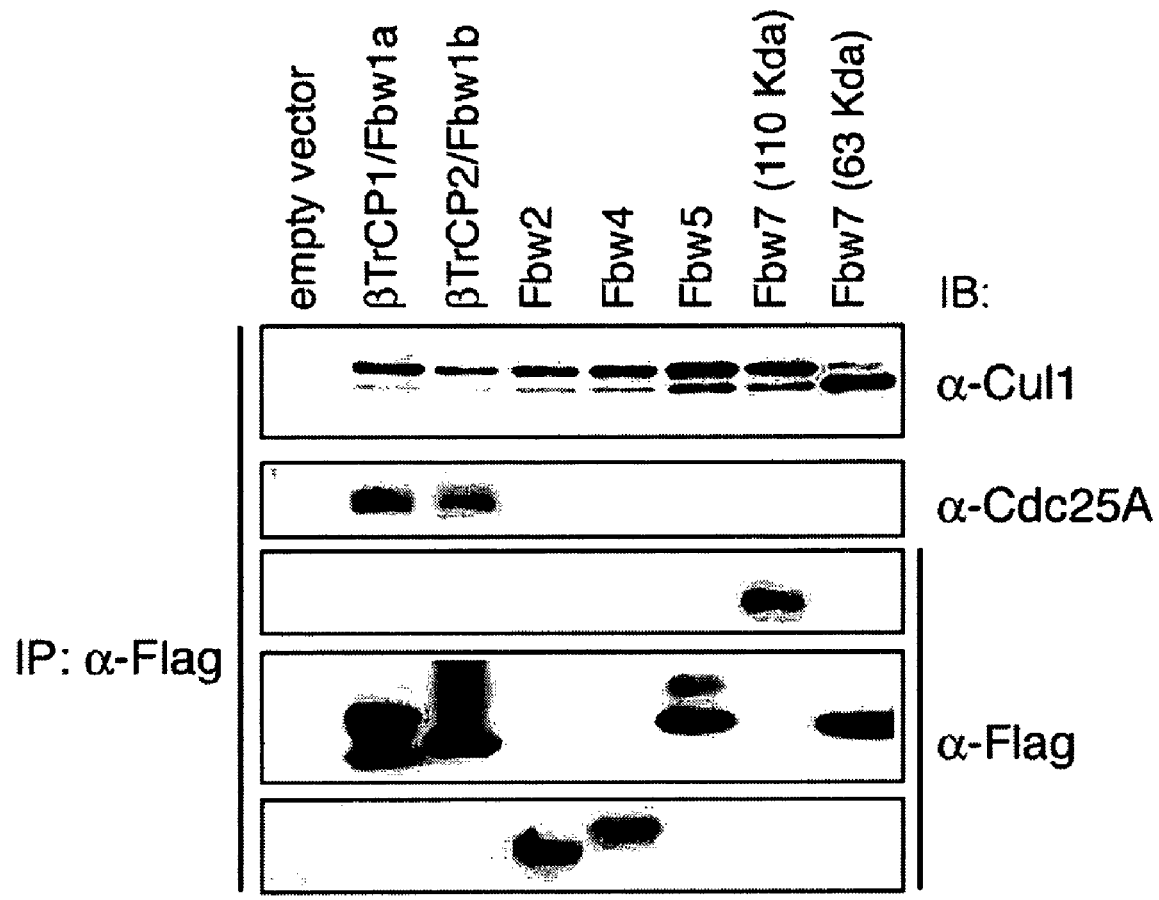
FIG. 1. Cdc25A interacts with beta-TrCP1 and beta-TrCP2 in vivo (I). HeLa cells were transfected with the indicated Flag-tagged F-box protein constructs. F-box proteins were immunoprecipitated from extracts with an anti-Flag resin and immunocomplexes were blotted with Cul1, Cdc25A and Flag specific antibodies.
Figure 2:
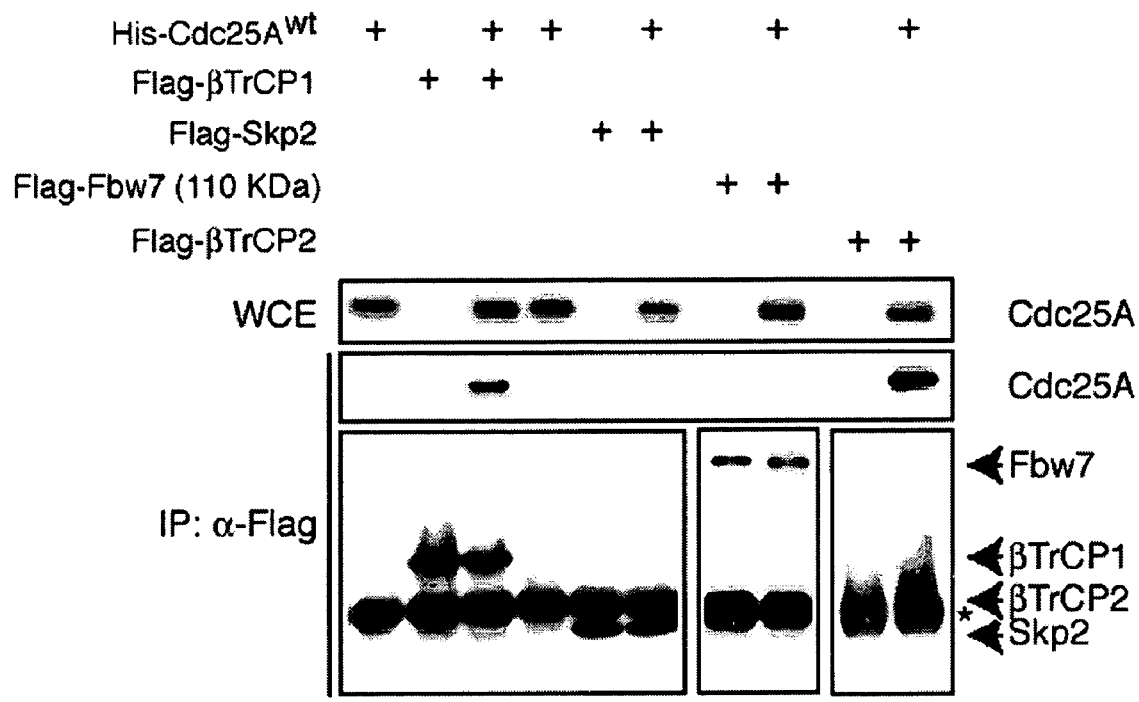
FIG. 2. Cdc25A interacts with beta-TrCP1 and beta-TrCP2 in vivo (II). HeLa cells were co-transfected with His-Cdc25A expressing vector and the indicated Flag-tagged F-box protein constructs. Immunocomplexes were analyzed as in FIG.

It was observed that β-TrCP1 and β-TrCP2 were the only F-box proteins among those tested which were able to interact with Cdc25A in vivo (FIG. 1). In a parallel experiment, it was shown that overexpressed Cdc25A co-precipitates with β-TrCP1 and β-TrCP2, but not with Skp2 and Fbw7 (FIG. 2). Interestingly, the Cdc25A co-precipitating with beta-TrCP was hyperphosphorylated, since treatment of the immunocomplexes with λ-phosphatase generated a faster migrating Cdc25A band (FIG. 3).

Example 2

Motifs Contributing to Cdc25A/β-TrCP Interaction

The Cdc25A amino acid sequence contains a motif, DSGXXXXS (SEQ ID NO:20), similar to the DSGXXS (SEQ ID NO:21) or DSGXXXS (SEQ ID NO:22) present in known protein substrates of the $SCF^{\beta-TrCP}$ complex (FIG. 4; Yaron, A. et al., Nature, 1998;396: 590-4; Winston, J. T. et al., Genes Dev, 1999;13:270-83; Lassot, I. et al., Mol Cell Biol, 2001;21:2192-202; and Lang, V. et al., Mol Cell Biol, 2003; 23:402-13). Phosphorylation at both serine residues is required for beta-TrCP binding and for subsequent substrate degradation to occur (Winston, J. T. et al., Genes Dev, 1999; 13:270-83; Liu, C. et al., Cell, 2002;108:837-47).

To assess the contribution of this motif to the interaction, both Ser82 and Ser88 were mutated to Ala to generate a mutant called DSG2x, and Ser82, Ser88, and Ser79 were mutated to Ala to produce a mutant called DSG3x (FIG. 4). It was then tested whether the mutated proteins would interact with beta-TrCP in transfected cells. As shown in FIG. 5, replacement of DSG(x)4S serine residues with alanine residues was sufficient to abolish Cdc25A interaction with β-TrCP1.

The Cdc25A interaction with β-TrCP1 is likely dependent upon phosphorylation on the DSG(x)4S serine residues. Indeed, a Cdc25A-derived peptide containing phosphoserine residues at positions Ser82 and Ser88 (depicted in FIG. 4) associated with in vitro-translated β-TrCP1 and β-TrCP2, but not with other F-box proteins tested, whereas the unphosphorylated peptide failed to associate at all (FIG. 6).

It was then assessed whether a failure to interact with β-TrCP would affect the stability of Cdc25A, by determining the respective half-lives of the $Cdc25A^{DSG2x}$ and $Cdc25A^{DSG3x}$ mutants. It was found that the mutants were significantly stabilized as compared to the wild type (FIG. 7).

To investigate whether β-TrCP stimulates Cdc25A ubiquitylation, an in vitro-ubiquitylation assay using partially reconstituted HeLa cell extracts was performed. As shown in FIG. 8, addition of recombinant purified β-TrCP1, but not of two other F-box proteins, Skp2 or Fbw7, stimulated Cdc25A ubiquitylation. Furthermore, ubiquitylation by beta-TrCP requires protein phosphorylation, since the reaction was inhibited by replacing ATP with AMP-PNP, an analog that allows ubiquitin adenylation by E1 but cannot serve as a protein kinase substrate (FIG. 9). As a control, it was observed that AMP-PNP could support APC-dependent ubiquitylation, which does not require substrate phosphorylation. These data support the hypothesis that Cdc25A phosphorylation is required for beta-TrCP-mediated ubiquitylation. Notably, it was also found that β-TrCP1-mediated ubiquitylation of the $Cdc25A^{DSG3x}$ mutated protein was greatly affected compared to the wild type (FIG. 10).

Altogether, these data show that phosphorylation on Ser82 and Ser88 is required for efficient Cdc25A recruitment by β-TrCP and subsequent Cdc25A degradation.

Example 3

Effect of β-TrCP Silencing on Cdc25A Accumulation

To conclusively assess the role of β-TrCP proteins in controlling the subcellular abundance of Cdc25A, a series of siRNA experiments were performed. Briefly, asynchronously growing cells were transiently transfected with a small interfering RNA oligonucleotide targeting both beta-TrCPI and beta-TrCP2 genes and analyzed for levels of Cdc25A at steady state. As shown in FIG. 11, efficient silencing of β-TrCP1 and β-TrCP2 genes caused a substantial accumulation of Cdc25A as compared to mock-transfected cells. No significant changes were observed on Cdc25A mRNA level (FIG. 12).

With this data at hand, the consequences of silencing β-TrCP gene expression at various stages of the cell cycle were tested. Mock or β-TrCP1/2 siRNA-transfected cells were synchronized by double-thymidine treatment, released from G1/S arrest in the presence of nocodazole and followed over time for Cdc25A accumulation. β-TrCP1/2 siRNA-treated cells progressing through S phase showed a substantial accumulation of Cdc25A as compared to mock-transfected cells, as well as a failure to degrade the APC inhibitor Emi1 (also known as Fbx5), a recently identified target of β-TrCP at early mitosis (FIG. 12; Guardavaccaro, D. et al., Dev Cell, 2003;4:799-812; Margottin-Goguet, F. et al., Dev Cell, 2003;4:813-26).

To analyze the kinetics of Cdc25A expression at mitotic exit and in G1-phase, mock or β-TrCP1/2 siRNA-transfected cells were synchronized by nocodazole treatment, released from the mitotic block and analyzed over time for Cdc25A expression. β-TrCP1/2 siRNA-transfected cells had a substantially higher level of Cdc25A at mitosis compared to mock-transfected cells, but, resembling control cells, they proceeded normally into G1 phase and degraded both Cdc25A and cyclin B1, even if with a slower kinetics (FIG. 13). This behavior is likely caused by the increased level of Emi1 in β-TrCP siRNA-transfected cells (Guardavaccaro, D. et al., supra; Margottin-Goguet, F. et al., supra), resulting in an indirect upregulation of Cdc25A through inhibition of Cdh1 at the exit of mitosis (Hsu, J. Y., et al., Nat Cell Biol, 2002;4:358-66).

Direct comparison of Cdc25A levels in mock, beta-TrCP1/2 and Emi1 siRNA-transfected cells at different time points is reported in FIGS. 12 and 13 (right panels). Remarkably, elimination of beta-TrCP caused an accumulation of Cdc25A in all cell cycle phases, with the exception of G1 (T6 in FIG. 13). As a control, it was assessed that elimination of Emi1 did not affect Cdc25A protein expression. Additionally, it was observed that the $Cdc25A^{KEN2}$ mutant, that fails to be degraded by $APC/C^{Cdh1}$, also accumulated in β-TrCP1/2 siRNA-transfected cells (FIG. 14).

Altogether, these data show that beta-TrCP-mediated degradation of Cdc25A occurs through S and G2, and that this event is independent from the release of the Emi1-mediated inhibition of Cdh1.

Example 4

Effect of β-TrCP Silencing on Response to DNA Damage

To examine whether β-TrCP proteins are involved in the ubiquitin-mediated degradation of Cdc25A in response to DNA damage, β-TrCP1/2 siRNA-transfected cells were treated with ionizing radiation (IR) and analyzed for Cdc25A abundance. Cells with reduced β-TrCP1/2 showed elevated Cdc25A levels compared to mock-transfected and Cdh1-depleted cells, used as a negative control. Notably, the IR-treatment resulted in an accumulation of slow-migrating, hyperphosphorylated Cdc25A species (FIGS. 15 and 16). Furthermore, the half-life of the protein in S-phase-synchronized and β-TrCP1/2-depleted cells was extended and remained unmodified in IR-treated compared to untreated cells (FIG. 16).

To establish a role for β-TrCP in the Cdc25A-mediated DNA damage responses, it was examined whether interfering with β-TrCP would result in a defect in the temporal inhibition of DNA synthesis. Radioresistant DNA synthesis (RDS), a phenotype indicative of a defective intra-S-phase checkpoint, occurs in cells deficient for ATM and Chk2, both upstream negative effectors of Cdc25A abundance (Falck, J., et al., Nature, 2001;410:842-7); Painter, R. B. et al., Proc Natl Acad Sci USA, 1980;77:7315-7). The integrity of the intra-S-phase checkpoint in beta-TrCP siRNA-transfected cells was checked by assessing the DNA synthesis rate after IR treatment. Whereas mock-transfected cells showed an inhibition of DNA synthesis after IR of approximately 40-50%, β-TrCP1/2-depleted cells reduced the inhibitory effects to roughly 20%, consistent with a radiosensitive (RDS) phenotype (FIG. 17). This effect is dependent on Cdc25A accumulation caused by β-TrCP inhibition, given that cells depleted for both beta-TrCP and Cdc25A rescued the RDS phenotype.

Using a polyclonal antibody raised against the phosphorylated DSG motif of Cdc25A (phosphoSer82/Ser88) and phosphopeptide mapping, we could detect Cdc25A phosphorylation at the DSG in cycling cells. As shown in FIG. 18, DSG phosphorylation was stimulated upon IR-treatment. It appears therefore that Cdc25A is phosphorylated at the DSG motif in cycling cells and that this process is enhanced upon DNA damage. Expression of the DSG2x protein did, in fact, hamper Cdc25A degradation upon IR-treatment (FIG. 19).

Recently, it has been shown that Cdc25A is phosphorylated on specific serine residues by the Chk1 protein kinase in cycling cells and by both Chk1 and Chk2 in checkpoint activated cells (Sorensen, C. S. et al., Cancer Cell, 2003;3:247-58) and that disruption of the Chk1/Cdc25A pathway abrogates ionizing radiation-induced S and G2 checkpoints (Zhao, H., et al., Proc Natl Acad Sci USA, 2002;24:24; Sorensen, C. S. et al., supra). Combined mutation of these residues confers stability to the protein, thus suggesting that phosphorylation at multiple sites contributes to Cdc25A degradation in vivo (Sorensen, C. S. et al., supra). These findings might indicate that, as is the case for the recognition of Sic1 by the Fbw7 protein (Verma, R. et al., Science, 1997;278:455-60), multiple phosphorylation events on the target protein enhance its interaction with the F-box protein and stimulate its polyubiquitylation (Nash, P. et al., Nature, 2001;414:514-21). In the case of Cdc25A, we found that while the DSG2x mutated protein failed to form complexes in vivo with β-TrCP1, Skp1 or Cul1, none of the Chk1/2 phosphorylation site mutants were impaired in binding these SCF components (FIG. 20). The finding that the β-TrCP phospho-degron (phosphorylated target sequence) is required for beta-TrCP binding (FIG. 20) and for beta-TrCP-dependent ubiquitylation (FIG. 10) imposes that efficient Cdc25A recognition by beta-TrCP minimally requires two phosphorylation sites in Cdc25A. This is in agreement with the recently published three-dimensional structure of a beta-TrCP1-Skp1-beta-catenin complex (Wu, G., et al., Mol Cell, 2003;11:1445-56). Phosphorylation on serine residues other than those of the DSG, might stimulate the degradation of Cdc25A by providing an interaction with additional components of the SCF complex, or by enhancing the ability of SCF to catalyze polyubiquitylation.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of screening for an agent useful for sensitizing a cancer cell to DNA damage by a second agent, which comprises:
   (i) contacting a human β-transducin repeat containing protein (β-TrCP) β-TrCP1 or β-TrCP2 with a test compound and a phosphorylated cell division cycle 25A (Cdc25A) protein or a phosphorylated fragment thereof of at least 8 amino acids in length;
   (ii) detecting a reduced binding of the β-TrCP1 or β-TrCP2 to the phosphorylated Cdc25A protein or fragment thereof in the presence of the test compound as compared to a control; and
   (iii) selecting the test compound that reduces the binding as an agent useful for sensitizing a cancer cell to DNA damage by the second agent;
   wherein the control is the binding of the β-TrCP1 or β-TrCP2 to the Cdc25A protein or fragment thereof in the absence of the test compound.

2. The method of claim 1, wherein the β-TrCP1 comprises the sequence of SEQ ID NO:3.

3. The method of claim 1, wherein the β-TrCP2 comprises the sequence of SEQ ID NO:6.

4. The method of claim 1, wherein the Cdc25A protein or fragment thereof comprises the sequence of SEQ ID NO:29.

5. The method of claim 4, wherein the Cdc25A protein comprises the sequence of SEQ ID NO:8.

6. The method of claim 1, wherein the second agent is ionizing radiation or an alkylating agent.

7. The method of claim 1, wherein the β-TrCP1 or β-TrCP2 and Cdc25A protein or fragment thereof are expressed by a cell, and the test compound is added to the cell.

8. The method of claim 1, wherein the β-TrCP1 or β-TrCP2, test compound, and phosphorylated Cdc25A protein or fragment thereof are in a reconstituted system.

9. The method of claim 7, wherein the cell further expresses Skp1 and Cul1.

10. The method of claim 8, wherein the reconstituted system further comprises Skp1 and Cul1.

* * * * *

```
                        SEQUENCE LISTING

<160> NUMBER OF SEQ ID NOS: 29

<210> SEQ ID NO 1
<211> LENGTH: 6146
<212> TYPE: DNA
<213> ORGANISM: Homo sapiens

<400> SEQUENCE: 1
taagagaggg cgggggaag gaagaggagg cgggatccgg gcgctgcgtt ggctgcggcc        60
tggcaccaaa ggggcggccc cggcggagag cggacccagt ggcctcggcg attatggacc      120
cggccgaggc ggtgctgcaa gagaaggcac tcaagtttat gtgctctatg cccaggtctc      180
tgtggctggg ctgctccagc ctggcggaca gcatgccttc gctgcgatgc ctgtataacc      240
cagggactgg cgcactcaca gctttccaga attcctcaga gagagaagac tgtaataatg      300
gcgaaccccc taggaagata ataccagaga agaattcact tagacagaca tacaacagct      360
gtgccagact ctgcttaaac caagaaacag tatgtttagc aagcactgct atgaagactg      420
agaattgtgt ggccaaaaca aaacttgcca atggcacttc cagtatgatt gtgcccaagc      480
aacggaaact ctcagcaagc tatgaaaagg aaaaggaact gtgtgtcaaa tactttgagc      540
agtggtcaga gtcagatcaa gtggaatttg tggaacatct tatatcccaa atgtgtcatt      600
accaacatgg gcacataaac tcgtatctta aacctatgtt gcagagagat ttcataactg      660
ctctgccagc tcggggattg gatcatattg ctgagaacat tctgtcatac ctggatgcca      720
aatcactatg tgctgctgaa cttgtgtgca aggaatggta ccgagtgacc tctgatggca      780
tgctgtggaa gaagcttatc gagagaatgg tcaggacaga ttctctgtgg agaggcctgg      840
cagaacgaag aggatgggga cagtatttat tcaaaaacaa acctcctgac gggaatgctc      900
ctcccaactc tttttataga gcactttatc ctaaaattat acaagacatt gagacaatag      960
```

```
aatctaattg gagatgtgga agacatagtt tacagagaat tcactgccga agtgaaacaa    1020
gcaaaggagt ttactgttta cagtatgatg atcagaaaat agtaagcggc cttcgagaca    1080
acacaatcaa gatctgggat aaaaacacat tggaatgcaa gcgaattctc acaggccata    1140
caggttcagt cctctgtctc cagtatgatg agagagtgat cataacagga tcatcggatt    1200
ccacggtcag agtgtgggat gtaaatacag gtgaaatgct aaacacgttg attcaccatt    1260
gtgaagcagt tctgcacttg cgtttcaata atggcatgat ggtgacctgc tccaaagatc    1320
gttccattgc tgtatgggat atggcctccc caactgacat taccctccgg agggtgctgg    1380
tcggacaccg agctgctgtc aatgttgtag actttgatga caagtacatt gtttctgcat    1440
ctggggatag aactataaag gtatggaaca caagtacttg tgaatttgta aggaccttaa    1500
atggacacaa acgaggcatt gcctgtttgc agtacaggga caggctggta gtgagtggct    1560
catctgacaa cactatcaga ttatgggaca tagaatgtgg tgcatgttta cgagtgttag    1620
aaggccatga ggaattggtg cgttgtattc gatttgataa caagaggata gtcagtgggg    1680
cctatgatgg aaaaattaaa gtgtgggatc ttgtggctgc tttggacccc cgtgctcctg    1740
cagggacact ctgtctacgg acccttgtgg agcattccgg aagagttttt cgactacagt    1800
ttgatgaatt ccagattgtc agtagttcac atgatgacac aatcctcatc tgggacttcc    1860
taaatgatcc agctgcccaa gctgaacccc ccgttcccc ttctcgaaca tacacctaca    1920
tctccagata aataaccata cactgacctc atacttgccc aggacccatt aaagttgcgg    1980
tatttaacgt atctgccaat accaggatga gcaacaacag taacaatcaa actactgccc    2040
agtttccctg gactagccga ggagcagggc tttgagactc ctgttgggac acagttggtc    2100
tgcagtcggc ccaggacggt ctactcagca caactgactg cttcagtgct gctatcagaa    2160
gatgtcttct atcttttgtg aatgattgga acttttaaac ctcccctcct ctcctccttt    2220
cacctctgca cctagttttt tcccattggt tccagacaaa ggtgacttat aaatatattt    2280
agtgttttgc cagaatctct cttgctttgc cattaagcag aagaactagt ttccctgtat    2340
agcctgctgg gagagaccca cttctagggt atggggatg cagcttcaag cccagtgccc    2400
agtgtctccc tgttaactgc aggaatgcca agcacctggc cagagcagcc cagccccaat    2460
atgcttagga ggagacagag ttccctctgt atagcctctg ggacaagaaa aagaaaacac    2520
aagaatgtat acactggaag atttgggcct cctgcctgcc ttctctttgt ttctgttcct    2580
cttcccatct actcccctac gccccttcaa ccttttttct ctgtctgctt cacctgagaa    2640
gaaagtgtac gaagagagtg tcctcctctc acatgagcca gatcagccag aaaatgcaac    2700
acttggaaga gttaaatgct gttcagtgaa gatttcagcc ccaggccttt gctgcaagtg    2760
accctgtggc aacagtggat tctcagacat gatactctca tcatatttgc aactcttctc    2820
tctctttctt ccccacaccc aagaggagga ttggtggtag ggggcaggca gaggggtgg    2880 ggagaagttt cctgggctcc atcaatggct gcatcttttc tggactcagc agtctccttg    2940
attccatgta gagtgtggaa aggagttgct gattgcattt cctctcatta acaattgggt    3000
gtgtaataaa aagcattgta cttcatctta aatcactggt aaggctcagc ctacagaaag    3060
atttgaaatg ccagagcca atcgcttggt gcattctgcg taatggtttc catctccgat    3120
ttcctcatca gggcctgtga ataccaggt gcctgtatct ttgccaagac cgtgatcaag    3180
gtagcttaag agagatggtc aggagaaaac actgtttttg ttttttttgt tgttttgttt    3240
tgttttggcc agttaaatat catctctcaa atattgatct caccgtgtca accttgcact    3300
gcacaacctt ccttctgctt ctcccacacc cagtatttgc agaagggcaa agctgcttaa    3360
```

```
gagagaggat cagggtgaag tttggcacac agggtttatt aatggggcaa aaactgcctt   3420
ttcttcctcc tcctgacctt attttgctct tcactctccc cagccaataa agcgtctgtg   3480
gcgattggtg aacagcataa acagctggac ctcagcaagg gtcaggcaaa cccagtcact   3540
cggaaggcag ctgtgtgagc tgccaagcta gtgggcttca ggtgcaaggg tacctgtgcc   3600
acaccaacct gggagcacac agaatactat taatgtgcac ccagctggtc tccccaggca   3660
agaaggtatc ctcttcccaa ggtgtaccca ctgaatgttg ttactacata ttgagagtca   3720
ttttatgcat atgcattcta cctttcctgc tttatgagta tttttaagct tttagttcaa   3780
ggttatattc agaaaatatt tcccagtata atgatacatc gtagcctaag aaatattttc   3840
tcaatgtaat tcccttccca gctacccaaa tgctacagag aaatgttttc tacttggcca   3900
ctatcagggt tcgtcatcta ttgtgttgac tattaatggc ttttgattg ggtaaggatt   3960 ttgctataga tgaaggtaga gggctgtcag ccctgaaaaa cacacaggtc agacatttaa   4020
aaggcatggg tttcgagctg tctcaaaata ttgcccaata gccataattt taccagcctt   4080
tctgtcatat gctgctatta caaagtggaa gctgttgaat gtttattggt gcccagggtt   4140
ttgctctcca atctaggttc agttgaagga atattgtttc taagactgtt ttgagacatg   4200
tccagtacat cacaaaggag atcggggcga cccctgcaga tgtggagcca ttagcccagt   4260
tgaggatatt ctccaagttg tcctctctcc tgctgatgga aatgggaatg aagttaagtg   4320
gtctgaaaaa cttgaatcgt tcacatttct cagctctggg ggtcatttac cagtttgttg   4380
tagaagaaat aatcaggtaa gttaaaagtt catttccaga gaaggtaaac cccacttacc   4440
atctctgcat gatttcagtg ggaattgatt atcactaatc cccaactggg ctagaataaa   4500
tgtaaagttt gaccttttta aaacgaaaag agagacaaag tctcagcaca ttccaaggag   4560
tggtagaaac agagctgaag gtgtccccat tgtagattag tctcttctca ctaaaattta   4620 cttttccaacg tagggcctaa aggaaaacctt tcttaaagac aggctgaaac cccttcaaag   4680
gcagatgagg aggtacagac acgtgacctt tggtgcaca ctggagctac ttggacaaga   4740
ccagcatgcc ttgctgcacg tgtgtgtatt tcactgctga aacatccctt taacttggtg   4800
tgcaatttga aaggatgtga atcatggatg gaaggccatt tgtacatgtc ccttggcaaa   4860 attcttctg gtgtctccta acttcagaga cagggactct ttttggatct ctattgacaa   4920
gtaataaaag tctggccctc ataacttgtt tccgaactag aaaagtctgt gagaccccta   4980
catcattctg gttttttgc ttgagtaaga acaatccttt tttattttc ttctgtacag   5040 tctaaagcta cagagaaaaa aaaatgcact cttcccttgc cggctcctgg taccattggt   5100
ctgaacagct gtagttggtc tactccttac ttagcacttg attgtgtggg gaaacaaagg   5160 tgggagggt ggggaatact ggaaataatc agggcaattt ttttctttcc cataattgga   5220
ctagatacct tggtactgtt gaccttctca gcatctccct tttgccttag atggcaacac   5280
cctccagtct gtagcagagc agtccaaccc agattagtgc agcccggagg cttagggtgc   5340
agcctccctg gtcttcctcc acacagttgt tcaccaacag accagacctc ctttaaccac   5400
agtgtcaaca tagtatcgga aagagagcca tttcttaggg gaataaaaca gtttcgcttc   5460
tttagctcat ctgtggtgtc agaatccttg gagctgaaga gagaaatcaa aagagcatga   5520
tgatggctgc ctggtttcag gtggaactta atgcattgat ctttagaagc tccttctgtt   5580
ggaagttgag tacctgtgat ctaaaatgtc ctggaggcag atgacatcta aaatatgtgc   5640
tttccaacca gcacagctgg cgctcttagc tcctgattgg ttgtgtgttt tattaaggat   5700
```

| | |
|---|---|
| cagtgcagtt aagtcgtatt ttaaagtgtt acctcccctc ctaacccttc cccttcttgg | 5760 |
| acactgaagg aaaaggccaa ctagggtgtt agccctctgg gcaccaagga aactaacagc | 5820 |
| tttctcaaag cggtgaccac tcaggccagc ccagacaaat ctgagggatg ccagtgcac | 5880 |
| tccaatgatg ggacaggcct aacaacacat gtaagcttcc ccgagagctt tcagctggtt | 5940 |
| cacctctttg ttctctagac tcttaagtac tgactgcttt gacttttgtg attatgttat | 6000 |
| ggtgatgtgt agtcagtgta ccaatatgtt cacaacctag gatcatgata atggagtgtg | 6060 |
| ttttgggttt tttttaactg ttcagaaaaa aagtaaatta caaatataag attaaagtga | 6120 |
| aaaaaaaaaa aaaaaaaaaa aaaaaa | 6146 |

<210> SEQ ID NO 2
<211> LENGTH: 2151
<212> TYPE: DNA
<213> ORGANISM: Homo sapiens

<400> SEQUENCE: 2

| | |
|---|---|
| tgcgttggct gcggcctggc accaaagggg cggccccggc ggagagcgga cccagtggcc | 60 |
| tcggcgatta tggaccccgg cgaggcggtg ctgcaagaga aggcactcaa gtttatgaat | 120 |
| tcctcagaga gagaagactg taataatggc gaacccccta ggaagataat accagagaag | 180 |
| aattcactta gacagacata caacagctgt gccagactct gcttaaacca agaaacagta | 240 |
| tgtttagcaa gcactgctat gaagactgag aattgtgtgg ccaaaacaaa acttgccaat | 300 |
| ggcacttcca gtatgattgt gcccaagcaa cggaaactct cagcaagcta tgaaaaggaa | 360 |
| aaggaactgt gtgtcaaata cttttgagcag tggtcagagt cagatcaagt ggaatttgtg | 420 |
| gaacatctta tatcccaaat gtgtcattac caacatgggc acataaactc gtatcttaaa | 480 |
| cctatgttgc agagagattt cataactgct ctgccagctc ggggattgga tcatatcgct | 540 |
| gagaacattc tgtcatacct ggatgccaaa tcactatgtg ctgctgaact tgtgtgcaag | 600 |
| gaatggtacc gagtgaccct tgatggcatg ctgtggaaga agcttatcga gagaatggtc | 660 |
| aggacagatt ctctgtggag aggcctggca gaacgaagag gatggggaca gtatttattc | 720 |
| aaaaacaaac ctcctgacgg gaatgctcct cccaactctt tttatagagc actttatcct | 780 |
| aaaattatac aagacattga gacaatagaa tctaattgga gatgtggaag acatagttta | 840 |
| cagagaattc actgccgaag tgaaacaagc aaaggagttt actgtttaca gtatgatgat | 900 |
| cagaaaatag taagcggcct tcgagacaac acaatcaaga tctgggataa aaacacattg | 960 |
| gaatgcaagc gaattctcac aggccataca ggttcagtcc tctgtctcca gtatgatgag | 1020 |
| agagtgatca taacaggatc atcggattcc acggtcagag tgtgggatgt aaatacaggt | 1080 |
| gaaatgctaa acacgttgat tcaccattgt gaagcagttc tgcacttgcg tttcaataat | 1140 |
| ggcatgatgg tgacctgctc caaagatcgt tccattgctg tatgggatat ggcctcccca | 1200 |
| actgacatta ccctccggag ggtgctggtc ggacaccgag ctgctgtcaa tgttgtagac | 1260 |
| tttgatgaca gtacattgt ttctgcatct ggggatagaa ctataaaggt atggaacaca | 1320 |
| agtacttgtg aatttgtaag gaccttaaat ggacacaaac gaggcattgc ctgtttgcag | 1380 |
| tacagggaca ggctggtagt gagtggctca tctgacaaca ctatcagatt atgggacata | 1440 |
| gaatgtggtg catgtttacg agtgttagaa ggccatgagg aattggtgcg ttgtattcga | 1500 |
| tttgataaca agaggatagt cagtggggcc tatgatggaa aaattaaagt gtgggatctt | 1560 |
| gtggctgctt tggaccccg tgctcctgca gggacactct gtctacggac ccttgtggag | 1620 |
| cattccggaa gagttttcg actacagttt gatgaattcc agattgtcag tagttcacat | 1680 |

-continued

```
gatgacacaa tcctcatctg ggacttccta aatgatccag ctgcccaagc tgaaccccccc    1740 cgttcccctt ctcgaacata cacctacatc tccagataaa taaccataca ctgacctcat    1800
acttgcccag gacccattaa agttgcggta tttaacgtat ctgccaatac caggatgagc    1860
aacaacagta acaatcaaac tactgcccag tttccctgga ctagccgagg agcagggctt    1920
tgagactcct gttgggacac agttggtctg cagtcggccc aggacggtct actcagcaca    1980
actgactgct tcagtgctgc tatcagaaga tgtcttctat caattgtgaa tgattggaac    2040
ttttaaacct cccctcctct cctcctttca cctctgcacc tagttttttc ccattggttc    2100
cagacaaagg tgacttataa atatatttag tgttttgcca gaaaaaaaaa a             2151
```

<210> SEQ ID NO 3
<211> LENGTH: 569
<212> TYPE: PRT
<213> ORGANISM: Homo sapiens

<400> SEQUENCE: 3

```
Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285
```

```
Ile Lys Ile Trp Asp Lys Asn Thr Leu Glu Cys Lys Arg Ile Leu Thr
290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
                340                 345                 350

Leu Arg Phe Asn Asn Gly Met Met Val Thr Cys Ser Lys Asp Arg Ser
                355                 360                 365

Ile Ala Val Trp Asp Met Ala Ser Pro Thr Asp Ile Thr Leu Arg Arg
370                 375                 380

Val Leu Val Gly His Arg Ala Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
                420                 425                 430

Ile Ala Cys Leu Gln Tyr Arg Asp Arg Leu Val Val Ser Gly Ser Ser
                435                 440                 445

Asp Asn Thr Ile Arg Leu Trp Asp Ile Glu Cys Gly Ala Cys Leu Arg
450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
                500                 505                 510

Arg Thr Leu Val Glu His Ser Gly Arg Val Phe Arg Leu Gln Phe Asp
                515                 520                 525

Glu Phe Gln Ile Val Ser Ser Ser His Asp Asp Thr Ile Leu Ile Trp
530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 4
<211> LENGTH: 2134
<212> TYPE: DNA
<213> ORGANISM: Homo sapiens

<400> SEQUENCE: 4
gcgatagccg cctccgcctc tgcccgcctc cgccgtcgcc tcctccgccc gggccgttcg      60
ctgctgcgcg gggagagcga ggcggggccg ccggggccgc catggagccc gactcggtga     120
ttgaggacaa gaccatcgag ctcatgataa gtaatggaac atcatctgtg atcgtctcca     180
gaaagaggcc atcagaagga aactatcaaa agaaaaaga cttgtgtatt aaatattttg      240
accagtggtc tgaatcagat caagtggaat tgtggaaca tcttatttca cgaatgtgtc     300
attatcagca tggacatatt aactcttacc tgaagcccat gttgcagcgg gactttatta     360
ccgctttacc agagcaaggc ttagatcaca tagcagaaaa cattctttcg tacctggatg     420
ccaggtctct gtgtgcagca gagctggtat gtaaagaatg cagcgagtg atctcagaag      480 gaatgctttg gaagaagctg attgaacgaa tggtacgcac tgatccccta tggaaaggac     540
```

-continued

| | |
|---|---|
| tttcagaaag aagagggtgg gatcagtacc tgtttaaaaa cagacccaca gatggccctc | 600 |
| caaattcatt ttataggtca ttatacccaa agattatcca ggatatagag actatagaat | 660 |
| ctaactggcg gtgtggacga cacaacttgc agaggattca gtgccgctct gaaaatagta | 720 |
| aaggtgtcta ctgtttacag tacgatgatg aaaaaattat cagtggccta cgagataatt | 780 |
| ctattaagat atgggataaa accagcctgg aatgtttgaa agtgttaaca ggacacacag | 840 |
| gctctgtcct ctgtctgcag tatgatgagc gtgtcattgt aactggctct tcagattcta | 900 |
| cggtgagagt gtgggatgtg aacacgggtg aagttcttaa cacattgatc caccacaatg | 960 |
| aggctgtatt gcacttacgc ttcagcaatg gactgatggt gacctgttcc aaggaccgct | 1020 |
| ccattgctgt gtgggacatg gcttctgcga ccgacatcac tttacgccgt gtcctggttg | 1080 |
| gccaccgggc tgccgtcaat gtagtagact ttgacgacaa gtacatcgtg tctgcctctg | 1140 |
| gtgacaggac catcaaagtc tggagcacga gcacctgtga atttgttcgt actctcaatg | 1200 |
| ggcacaagcg gggcattgcc tgtctccagt acagggatcg cctggttgtt agtggatcat | 1260 |
| cagataatac cattaggctc tgggatattg aatgtggtgc ctgtttaaga gtcctagagg | 1320 |
| gacatgaaga attggtccga tgcatccggt ttgataacaa gaggattgtc agtggggcct | 1380 |
| atgatgggaa aattaaagtt tgggacttgc aagctgctct tgaccctcga gccccagcaa | 1440 |
| gcacattgtg tttgcgcaca ttggtggaac attctggacg tgtgtttcgg ctccagtttg | 1500 |
| atgagtttca gatcatcagc agctcccatg atgacactat tttgatttgg gatttcttaa | 1560 |
| atgtgcctcc cagtgcccag aatgagaccc gttctccctc cagaacatac acttacatct | 1620 |
| ctagataaca gtctgcactt tcacccgttt cagggttttc tagtcttgaa ctactggcta | 1680 |
| cgtggctacc aaatgcctaa gggagttcgt tcacagctga gttatgaagc tggaattggt | 1740 |
| tctagacgct gggtagatgc aaagcagcct aactcttcaa gtaccgacat ttctcacctc | 1800 |
| tgattccggc tctcctttga gaaggagacc ttagcttccc cggcttcaag tagaacagaa | 1860 |
| gcccgtttcc ttccctcatc agtgaaaaaa tctaatgttt caaatgtaaa ttgttcatag | 1920 |
| aaaaggaaca tagaatctgt tttacagaag taaatcgacc gtcaagagaa gacttggcct | 1980 |
| ctaatttata ttgctttgca ctttggtttg atattaagaa acagcattct tcttcagtga | 2040 |
| aattttgggt gccaaacacc tacccagaat gtccagggct ttcattttca aaagttagca | 2100 |
| ttctcctttt gaccgtccaa gtcattatga attc | 2134 |

<210> SEQ ID NO 5
<211> LENGTH: 1653
<212> TYPE: DNA
<213> ORGANISM: Homo sapiens

<400> SEQUENCE: 5

| | |
|---|---|
| cgaggcgggg ccgccggggc cgccatggag cccgactcgg tgattgagga caagaccatc | 60 |
| gagctcatgt gttctgtgcc aaggtctttg tggctaggct gcgccaacct ggtagagagc | 120 |
| atgtgcgcac tgagttgcct gcagagcatg cccagtgtca gatgtctcca gataagtaat | 180 |
| ggaacatcat ctgtgatcgt ctccagaaag aggccatcag aaggaaacta tcaaaaagaa | 240 |
| aaagacttgt gtattaaata ttttgaccag tggtctgaat cagatcaagt ggaatttgtg | 300 |
| gaacatctta tttcacgaat gtgtcattat cagcatggac atattaactc ttacctgaag | 360 |
| cccatgttgc agcgggactt tattaccgct ttaccagagc aaggcttaga tcacatagca | 420 |
| gaaaacattc tttcgtacct ggatgccagg tctctgtgtg cagcagagct ggtatgtaaa | 480 |

-continued

```
gaatggcagc gagtgatctc agaaggaatg ctttggaaga agctgattga acgaatggta    540
cgcactgatc ccctatggaa aggactttca gaaagaagag ggtgggatca gtacctgttt    600
aaaaacagac ccacagatgg ccctccaaat tcattttata ggtcattata cccaaagatt    660
atccaggata tagagactat agaatctaac tggcggtgtg gacgacacaa cttgcagagg    720
attcagtgcc gctctgaaaa tagtaaaggt gtctactgtt tacagtacga tgatgaaaaa    780
attatcagtg gcctacgaga taattctatt aagatatggg ataaaaccag cctggaatgt    840
ttgaaagtgt taacaggaca cacaggctct gtcctctgtc tgcagtatga tgagcgtgtc    900
attgtaactg gctcttcaga ttctacggtg agagtgtggg atgtgaacac gggtgaagtt    960
cttaacacat tgatccacca caatgaggct gtattgcact tacgcttcag caatggactg   1020
atggtgacct gttccaagga ccgctccatt gctgtgtggg acatggcttc tgcgaccgac   1080
atcactttac gccgtgtcct ggttggccac cgggctgccg tcaatgtagt agactttgac   1140
gacaagtaca tcgtgtctgc ctctggtgac aggaccatca agtctggag cacgagcacc   1200 tgtgaatttg ttcgtactct caatgggcac aagcggggca ttgcctgtct ccagtacagg   1260
gatcgcctgg ttgttagtgg atcatcagat aataccatta ggctctggga tattgaatgt   1320
ggtgcctgtt taagagtcct agagggacat gaagaattgg tccgatgcat ccggtttgat   1380
aacaagagga ttgtcagtgg ggcctatgat gggaaaatta agtttggga cttgcaagct   1440 gctcttgacc ctcgagcccc agcaagcaca ttgtgtttgc gcacattggt ggaacattct   1500
ggacgtgtgt ttcggctcca gtttgatgag tttcagatca tcagcagctc ccatgatgac   1560
actattttga tttgggattt cttaaatgtg cctcccagtg cccagaatga gacccgttct   1620
ccctccagaa catacactta catctctaga taa                                1653

<210> SEQ ID NO 6
<211> LENGTH: 542
<212> TYPE: PRT
<213> ORGANISM: Homo sapiens

<400> SEQUENCE: 6

Met Glu Pro Asp Ser Val Ile Glu Asp Lys Thr Ile Glu Leu Met Cys
1               5                   10                  15

Ser Val Pro Arg Ser Leu Trp Leu Gly Cys Ala Asn Leu Val Glu Ser
            20                  25                  30

Met Cys Ala Leu Ser Cys Leu Gln Ser Met Pro Ser Val Arg Cys Leu
        35                  40                  45

Gln Ile Ser Asn Gly Thr Ser Ser Val Ile Val Ser Arg Lys Arg Pro
    50                  55                  60

Ser Glu Gly Asn Tyr Gln Lys Glu Lys Asp Leu Cys Ile Lys Tyr Phe
65                  70                  75                  80

Asp Gln Trp Ser Glu Ser Asp Gln Val Glu Phe Val Glu His Leu Ile
                85                  90                  95

Ser Arg Met Cys His Tyr Gln His Gly His Ile Asn Ser Tyr Leu Lys
            100                 105                 110

Pro Met Leu Gln Arg Asp Phe Ile Thr Ala Leu Pro Glu Gln Gly Leu
        115                 120                 125

Asp His Ile Ala Glu Asn Ile Leu Ser Tyr Leu Asp Ala Arg Ser Leu
    130                 135                 140

Cys Ala Ala Glu Leu Val Cys Lys Glu Trp Gln Arg Val Ile Ser Glu
145                 150                 155                 160

Gly Met Leu Trp Lys Lys Leu Ile Glu Arg Met Val Arg Thr Asp Pro
```

-continued

```
            165                 170                 175
Leu Trp Lys Gly Leu Ser Glu Arg Arg Gly Trp Asp Gln Tyr Leu Phe
        180                 185                 190

Lys Asn Arg Pro Thr Asp Gly Pro Asn Ser Phe Tyr Arg Ser Leu
        195                 200                 205

Tyr Pro Lys Ile Ile Gln Asp Ile Glu Thr Ile Glu Ser Asn Trp Arg
        210                 215                 220

Cys Gly Arg His Asn Leu Gln Arg Ile Gln Cys Arg Ser Glu Asn Ser
225                 230                 235                 240

Lys Gly Val Tyr Cys Leu Gln Tyr Asp Asp Glu Lys Ile Ile Ser Gly
                245                 250                 255

Leu Arg Asp Asn Ser Ile Lys Ile Trp Asp Lys Thr Ser Leu Glu Cys
                260                 265                 270

Leu Lys Val Leu Thr Gly His Thr Gly Ser Val Leu Cys Leu Gln Tyr
                275                 280                 285

Asp Glu Arg Val Ile Val Thr Gly Ser Ser Asp Ser Thr Val Arg Val
            290                 295                 300

Trp Asp Val Asn Thr Gly Glu Val Leu Asn Thr Leu Ile His His Asn
305                 310                 315                 320

Glu Ala Val Leu His Leu Arg Phe Ser Asn Gly Leu Met Val Thr Cys
                325                 330                 335

Ser Lys Asp Arg Ser Ile Ala Val Trp Asp Met Ala Ser Ala Thr Asp
                340                 345                 350

Ile Thr Leu Arg Arg Val Leu Val Gly His Arg Ala Ala Val Asn Val
                355                 360                 365

Val Asp Phe Asp Asp Lys Tyr Ile Val Ser Ala Ser Gly Asp Arg Thr
            370                 375                 380

Ile Lys Val Trp Ser Thr Ser Thr Cys Glu Phe Val Arg Thr Leu Asn
385                 390                 395                 400

Gly His Lys Arg Gly Ile Ala Cys Leu Gln Tyr Arg Asp Arg Leu Val
                405                 410                 415

Val Ser Gly Ser Ser Asp Asn Thr Ile Arg Leu Trp Asp Ile Glu Cys
                420                 425                 430

Gly Ala Cys Leu Arg Val Leu Glu Gly His Glu Glu Leu Val Arg Cys
                435                 440                 445

Ile Arg Phe Asp Asn Lys Arg Ile Val Ser Gly Ala Tyr Asp Gly Lys
            450                 455                 460

Ile Lys Val Trp Asp Leu Gln Ala Ala Leu Asp Pro Arg Ala Pro Ala
465                 470                 475                 480

Ser Thr Leu Cys Leu Arg Thr Leu Val Glu His Ser Gly Arg Val Phe
                485                 490                 495

Arg Leu Gln Phe Asp Glu Phe Gln Ile Ile Ser Ser Ser His Asp Asp
                500                 505                 510

Thr Ile Leu Ile Trp Asp Phe Leu Asn Val Pro Pro Ser Ala Gln Asn
            515                 520                 525

Glu Thr Arg Ser Pro Ser Arg Thr Tyr Thr Tyr Ile Ser Arg
        530                 535                 540

<210> SEQ ID NO 7
<211> LENGTH: 2419
<212> TYPE: DNA
<213> ORGANISM: Homo sapiens

<400> SEQUENCE: 7
```

-continued

```
cgaaaggccg gccttggctg cgacagcctg ggtaagaggt gtaggtcggc ttggttttct      60
gctacccgga gctgggcaag cgggttggga gaacagcgaa gacagcgtga gcctgggccg     120
ttgcctcgag gctctcgccc ggcttctctt gccgacccgc cacgtttgtt tggatttaat     180
cttacagctg gttgccggcg cccgcccgcc cgctggcctc gcggtgtgag agggaagcac     240
ccgtgcctgt ggctggtggc tggcgcctgg agggtccgca cacccgcccg gccgcgccgc     300
tttgcccgcg gcagccgcgt ccctgaaccg cggagtcgtg tttgtgtttg acccgcgggc     360
gccggtggcg cgcggccgag gccggtgtcg gcggggcggg gcggtcgcgg cggaggcaga     420
ggaagaggga gcgggagctc tgcgaggccg ggcgccgcca tggaactggg cccgagcccc     480
gcaccgcgcc gcctgctctt cgcctgcagc ccccctcccg cgtcgcagcc cgtcgtgaag     540
gcgctatttg gcgcttcagc cgccggggga ctgtcgcctg tcaccaacct gaccgtcact     600
atggaccagc tgcagggtct gggcagtgat tatgagcaac cactggaggt gaagaacaac     660
agtaatctgc agagaatggg ctcctccgag tcaacagatt caggtttctg tctagattct     720
cctgggccat tggacagtaa agaaaacctt gaaaatccta tgagaagaat acattccctg     780
cctcaaaagc tgttgggatg tagtccagct ctgaagagga gccattctga ttctcttgac     840
catgacatct ttcagctcat cgacccagat gagaacaagg aaaatgaagc ctttgagttt     900
aagaagccag taagacctgt atctcgtggc tgcctgcact tcatggact ccaggagggt      960 aaagatctct tcacacagag gcagaactct gcccagctcg gaatgctttc ctcaaatgaa    1020
agagatagca gtgaaccagg gaatttcatt cctctttttta cacccccagtc acctgtgaca    1080 gccactttgt ctgatgagga tgatggcttc gtggaccttc tcgatggaga gaatctgaag    1140
aatgaggagg agacccccct gtgcatggca agcctctgga cagctcctct cgtcatgaga    1200
actacaaacc ttgacaaccg atgcaagctg tttgactccc cttccctgtg tagctccagc    1260
actcggtcag tgttgaagag accagaacgt tctcaagagg agtctccacc tggaagtaca    1320
aagaggagga agagcatgtc tggggccagc cccaaagagt caactaatcc agagaaggcc    1380
catgagactc ttcatcagtc tttatccctg gcatcttccc ccaaaggaac cattgagaac    1440
attttggaca atgacccaag ggaccttata ggagacttct ccaagggtta tctctttcat    1500
acagttgctg ggaaacatca ggattttaaaa tacatctctc cagaaattat ggcatctgtt    1560
ttgaatggca agtttgccaa cctcattaaa gagtttgtta tcatcgactg tcgataccca    1620
tatgaatacg agggaggcca catcaagggt gcagtgaact gcacatggga agaagaggtt    1680
gaagacttct tattgaagaa gcccattgta cctactgatg gcaagcgtgt cattgttgtg    1740
tttcactgcg agttttcttc tgagagaggt ccccgcatgt gccggtatgt gagagagaga    1800
gatcgcctgg gtaatgaata ccccaaactc cactaccctg agctgtatgt cctgaagggg    1860
ggatacaagg agttctttat gaaatgccag tcttactgtg agcccctag ctaccggccc      1920 atgcaccacg aggactttaa agaagacctg aagaagttcc gcaccaagag ccggacctgg    1980
gcaggggaga agagcaagag ggagatgtac agtcgtctga gaagctctg agggcggcag      2040 gaccagccag cagcagccca agcttccctc catccccctt taccctcttt cctgcagaga    2100
aacttaagca aaggggacag ctgtgtgaca tttggagagg gggcctggga cttccatgcc    2160
ttaaacctac ctcccacact cccaaggttg agcccaggg catcttgctg gctacgcctc     2220
ttctgtccct gttagacgtc ctccgtccat atcagaactg tgccacaatg cagttctgag    2280
caccgtgtca agctgctctg agccacagtg ggatgaacca gccggggcct tatcgggctc    2340
cagcatctca tgaggggaga ggagacggag gggagtagag aagtttacac agaaatgctg    2400
```
ctggccaaat agcaaagag                                                                    2419

<210> SEQ ID NO 8
<211> LENGTH: 523
<212> TYPE: PRT
<213> ORGANISM: Homo sapiens

<400> SEQUENCE: 8

Met Glu Leu Gly Pro Ser Pro Ala Pro Arg Leu Leu Phe Ala Cys
1               5                   10                  15

Ser Pro Pro Ala Ser Gln Pro Val Val Lys Ala Leu Phe Gly Ala
                20                  25                  30

Ser Ala Ala Gly Gly Leu Ser Pro Val Thr Asn Leu Thr Val Thr Met
            35                  40                      45

Asp Gln Leu Gln Gly Leu Gly Ser Asp Tyr Glu Gln Pro Leu Glu Val
        50                  55                      60

Lys Asn Asn Ser Asn Leu Gln Arg Met Gly Ser Glu Ser Thr Asp
65                  70                  75                  80

Ser Gly Phe Cys Leu Asp Ser Pro Gly Pro Leu Asp Ser Lys Glu Asn
                85                  90                  95

Leu Glu Asn Pro Met Arg Arg Ile His Ser Leu Pro Gln Lys Leu Leu
                100                 105                 110

Gly Cys Ser Pro Ala Leu Lys Arg Ser His Ser Asp Ser Leu Asp His
                115                 120                 125

Asp Ile Phe Gln Leu Ile Asp Pro Asp Glu Asn Lys Glu Asn Glu Ala
130                 135                 140

Phe Glu Phe Lys Lys Pro Val Arg Pro Val Ser Arg Gly Cys Leu His
145                 150                 155                 160

Ser His Gly Leu Gln Glu Gly Lys Asp Leu Phe Thr Gln Arg Gln Asn
                165                 170                 175

Ser Ala Gln Leu Gly Met Leu Ser Ser Asn Glu Arg Asp Ser Ser Glu
                180                 185                 190

Pro Gly Asn Phe Ile Pro Leu Phe Thr Pro Gln Ser Pro Val Thr Ala
                195                 200                 205

Thr Leu Ser Asp Glu Asp Asp Gly Phe Val Asp Leu Leu Asp Gly Glu
210                 215                 220

Asn Leu Lys Asn Glu Glu Glu Thr Pro Ser Cys Met Ala Ser Leu Trp
225                 230                 235                 240

Thr Ala Pro Leu Val Met Arg Thr Thr Asn Leu Asp Asn Arg Cys Lys
                245                 250                 255

Leu Phe Asp Ser Pro Ser Leu Cys Ser Ser Thr Arg Ser Val Leu
                260                 265                 270

Lys Arg Pro Glu Arg Ser Gln Glu Glu Ser Pro Pro Gly Ser Thr Lys
                275                 280                 285

Arg Arg Lys Ser Met Ser Gly Ala Ser Pro Lys Glu Ser Thr Asn Pro
                290                 295                 300

Glu Lys Ala His Glu Thr Leu His Gln Ser Leu Ser Leu Ala Ser Ser
305                 310                 315                 320

Pro Lys Gly Thr Ile Glu Asn Ile Leu Asp Asn Asp Pro Arg Asp Leu
                325                 330                 335

Ile Gly Asp Phe Ser Lys Gly Tyr Leu Phe His Thr Val Ala Gly Lys
                340                 345                 350

His Gln Asp Leu Lys Tyr Ile Ser Pro Glu Ile Met Ala Ser Val Leu
                355                 360                 365

```
Asn Gly Lys Phe Ala Asn Leu Ile Lys Glu Phe Val Ile Ile Asp Cys
        370                 375                 380
Arg Tyr Pro Tyr Glu Tyr Gly Gly His Ile Lys Gly Ala Val Asn
385                 390                 395                 400
Leu His Met Glu Glu Val Glu Asp Phe Leu Lys Lys Pro Ile
                405                 410                 415
Val Pro Thr Asp Gly Lys Arg Val Ile Val Phe His Cys Glu Phe
                420                 425                 430
Ser Ser Glu Arg Gly Pro Arg Met Cys Arg Tyr Val Arg Glu Arg Asp
                435                 440                 445
Arg Leu Gly Asn Glu Tyr Pro Lys Leu His Tyr Pro Glu Leu Tyr Val
    450                 455                 460
Leu Lys Gly Gly Tyr Lys Glu Phe Phe Met Lys Cys Gln Ser Tyr Cys
465                 470                 475                 480
Glu Pro Pro Ser Tyr Arg Pro Met His His Glu Asp Phe Lys Glu Asp
                485                 490                 495
Leu Lys Lys Phe Arg Thr Lys Ser Arg Thr Trp Ala Gly Glu Lys Ser
                500                 505                 510
Lys Arg Glu Met Tyr Ser Arg Leu Lys Lys Leu
                515                 520

<210> SEQ ID NO 9
<211> LENGTH: 17
<212> TYPE: PRT
<213> ORGANISM: Homo sapiens

<400> SEQUENCE: 9

Trp Gln Gln Gln Ser Tyr Leu Asp Ser Gly Ile His Ser Gly Ala Thr
1               5                   10                  15
Thr

<210> SEQ ID NO 10
<211> LENGTH: 17
<212> TYPE: PRT
<213> ORGANISM: Homo sapiens

<400> SEQUENCE: 10

Arg Leu Leu Asp Asp Arg His Asp Ser Gly Leu Asp Ser Met Lys Asp
1               5                   10                  15
Glu

<210> SEQ ID NO 11
<211> LENGTH: 17
<212> TYPE: PRT
<213> ORGANISM: Homo sapiens

<400> SEQUENCE: 11

Ala Asp Ala Asp Glu Trp Cys Asp Ser Gly Leu Gly Ser Leu Gly Pro
1               5                   10                  15
Asp

<210> SEQ ID NO 12
<211> LENGTH: 17
<212> TYPE: PRT
<213> ORGANISM: Homo sapiens

<400> SEQUENCE: 12

Glu Ala Glu Glu Ser Gln Tyr Asp Ser Gly Ile Glu Ser Leu Arg Ser
```

-continued

```
1               5                   10                  15
Leu

<210> SEQ ID NO 13
<211> LENGTH: 17
<212> TYPE: PRT
<213> ORGANISM: Homo sapiens

<400> SEQUENCE: 13

Glu Thr Ser Arg Leu Tyr Glu Asp Ser Gly Tyr Ser Ser Phe Ser Leu
1               5                   10                  15

Gln

<210> SEQ ID NO 14
<211> LENGTH: 17
<212> TYPE: PRT
<213> ORGANISM: Homo sapiens

<400> SEQUENCE: 14

Arg Asp Ser Asp Ser Val Cys Asp Ser Gly Val Glu Thr Ser Phe Arg
1               5                   10                  15

Lys

<210> SEQ ID NO 15
<211> LENGTH: 17
<212> TYPE: PRT
<213> ORGANISM: Homo sapiens

<400> SEQUENCE: 15

Glu Asp Thr Pro Ser Asp Asn Asp Ser Gly Ile Cys Met Ser Pro Glu
1               5                   10                  15

Ser

<210> SEQ ID NO 16
<211> LENGTH: 23
<212> TYPE: PRT
<213> ORGANISM: Homo sapiens

<400> SEQUENCE: 16

Arg Met Gly Ser Ser Glu Ser Thr Asp Ser Gly Phe Cys Leu Asp Ser
1               5                   10                  15

Pro Gly Pro Leu Asp Ser Lys
                20

<210> SEQ ID NO 17
<211> LENGTH: 14
<212> TYPE: PRT
<213> ORGANISM: Homo sapiens

<400> SEQUENCE: 17

Thr Asp Ser Gly Phe Cys Leu Asp Ser Pro Gly Pro Leu Asp
1               5                   10

<210> SEQ ID NO 18
<211> LENGTH: 23
<212> TYPE: PRT
<213> ORGANISM: Artificial sequence
<220> FEATURE:
<223> OTHER INFORMATION: beta-TrCP1 mutant

<400> SEQUENCE: 18

Arg Met Gly Ser Ser Glu Ser Thr Asp Ala Gly Phe Cys Leu Asp Ala
```

-continued

```
                1               5                  10                 15
Pro Gly Pro Leu Asp Ser Lys
            20

<210> SEQ ID NO 19
<211> LENGTH: 23
<212> TYPE: PRT
<213> ORGANISM: Artificial sequence
<220> FEATURE:
<223> OTHER INFORMATION: beta-TrCP1 mutant

<400> SEQUENCE: 19

Arg Met Gly Ser Ser Glu Ala Thr Asp Ala Gly Phe Cys Leu Asp Ala
1               5                  10                 15

Pro Gly Pro Leu Asp Ser Lys
            20

<210> SEQ ID NO 20
<211> LENGTH: 6
<212> TYPE: PRT
<213> ORGANISM: Homo sapiens
<220> FEATURE:
<221> NAME/KEY: MISC_FEATURE
<222> LOCATION: (4)..(5)
<223> OTHER INFORMATION: X is any amino acid
<220> FEATURE:
<221> NAME/KEY: MISC_FEATURE
<222> LOCATION: (4)..(5)
<223> OTHER INFORMATION: Xaa is any amino acid

<400> SEQUENCE: 20

Asp Ser Gly Xaa Xaa Ser
1               5

<210> SEQ ID NO 21
<211> LENGTH: 7
<212> TYPE: PRT
<213> ORGANISM: Homo sapiens
<220> FEATURE:
<221> NAME/KEY: MISC_FEATURE
<222> LOCATION: (4)..(6)
<223> OTHER INFORMATION: Xaa is any amino acid

<400> SEQUENCE: 21

Asp Ser Gly Xaa Xaa Xaa Ser
1               5

<210> SEQ ID NO 22
<211> LENGTH: 8
<212> TYPE: PRT
<213> ORGANISM: Homo sapiens
<220> FEATURE:
<221> NAME/KEY: MISC_FEATURE
<222> LOCATION: (4)..(7)
<223> OTHER INFORMATION: X is any amino acid
<220> FEATURE:
<221> NAME/KEY: MISC_FEATURE
<222> LOCATION: (4)..(7)
<223> OTHER INFORMATION: Xaa is any amino acid

<400> SEQUENCE: 22

Asp Ser Gly Xaa Xaa Xaa Xaa Ser
1               5

<210> SEQ ID NO 23
<211> LENGTH: 21
<212> TYPE: DNA
<213> ORGANISM: Artificial sequence
```

```
<220> FEATURE:
<223> OTHER INFORMATION: beta-TrCP1 siRNA

<400> SEQUENCE: 23
cccagggacu ggcgcacuct t                                              21

<210> SEQ ID NO 24
<211> LENGTH: 21
<212> TYPE: DNA
<213> ORGANISM: Artificial sequence
<220> FEATURE:
<223> OTHER INFORMATION: beta-TrCP1 siRNA

<400> SEQUENCE: 24
uucucacagg ccauacaggt t                                              21

<210> SEQ ID NO 25
<211> LENGTH: 21
<212> TYPE: DNA
<213> ORGANISM: Artificial sequence
<220> FEATURE:
<223> OTHER INFORMATION: beta-TrCP2 siRNA

<400> SEQUENCE: 25
gaggccauca gaaggaaact t                                              21

<210> SEQ ID NO 26
<211> LENGTH: 21
<212> TYPE: DNA
<213> ORGANISM: Artificial sequence
<220> FEATURE:
<223> OTHER INFORMATION: beta-TrCP1/2 siRNA

<400> SEQUENCE: 26
guggaauuug uggaacauct t                                              21

<210> SEQ ID NO 27
<211> LENGTH: 21
<212> TYPE: DNA
<213> ORGANISM: Artificial sequence
<220> FEATURE:
<223> OTHER INFORMATION: cdh1 DNA sequence corresponding to siRNA

<400> SEQUENCE: 27
aatgagaagt ctcccagtca g                                              21

<210> SEQ ID NO 28
<211> LENGTH: 21
<212> TYPE: DNA
<213> ORGANISM: Artificial sequence
<220> FEATURE:
<223> OTHER INFORMATION: cdh1 DNA sequence corresponding to siRNA

<400> SEQUENCE: 28
aatctggtgg actggtcgtc c                                              21

<210> SEQ ID NO 29
<211> LENGTH: 14
<212> TYPE: PRT
<213> ORGANISM: Homo sapiens

<400> SEQUENCE: 29

Thr Asp Ser Gly Phe Cys Leu Asp Ser Pro Gly Pro Leu Asp
1               5                   10
```